(12) United States Patent
Van Nest et al.

(10) Patent No.: US 8,124,590 B2
(45) Date of Patent: Feb. 28, 2012

(54) BIODEGRADABLE IMMUNOMODULATORY FORMULATIONS AND METHODS FOR USE THEREOF

(75) Inventors: Gary Van Nest, Martinez, CA (US); Stephen F. Tuck, Oakland, CA (US); Karen L. Fearon, Lafayette, CA (US); Dino Dina, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 1241 days.

(21) Appl. No.: 11/820,592

(22) Filed: Jun. 19, 2007

(65) Prior Publication Data
US 2011/0038896 A1 Feb. 17, 2011

Related U.S. Application Data

(60) Division of application No. 09/927,422, filed on Aug. 10, 2001, now Pat. No. 7,250,403, which is a continuation-in-part of application No. 09/802,359, filed on Mar. 9, 2001, now abandoned.

(60) Provisional application No. 60/188,303, filed on Mar. 10, 2000.

(51) Int. Cl.
*A61K 39/00* (2006.01)
*A61K 48/00* (2006.01)
*A61K 47/00* (2006.01)
*A61K 38/00* (2006.01)
*A61K 39/38* (2006.01)
*A61K 45/00* (2006.01)
*A61K 9/127* (2006.01)
*A61K 39/385* (2006.01)

(52) U.S. Cl. ............... 514/44 R; 424/184.1; 424/278.1; 424/450; 424/193.1; 424/194.1

(58) Field of Classification Search .................. None
See application file for complete search history.

(56) References Cited

U.S. PATENT DOCUMENTS
4,458,006 A  7/1984  Dönges et al.
(Continued)

FOREIGN PATENT DOCUMENTS
EP  0 468 520 A2  1/1992
(Continued)

OTHER PUBLICATIONS

Higgins et al, J. Allergy and Clin. Immunol., 2006, 118/2:504-510.*

(Continued)

*Primary Examiner* — Nita M Minnifield
(74) *Attorney, Agent, or Firm* — Morrison & Foerster LLP

(57) ABSTRACT

The invention provides new compositions and methods for immunomodulation of individuals. Immunomodulation is accomplished by administration of immunomodulatory polynucleotide/microcarrier (IMP/MC) complexes. The IMP/MC complexes may be covalently or non-covalently bound, and feature a polynucleotide comprising at least one immunostimulatory sequence bound to a biodegradable microcarrier or nanocarrier.

23 Claims, No Drawings

U.S. PATENT DOCUMENTS

| | | | |
|---|---|---|---|
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,391,723 A | 2/1995 | Priest | |
| 5,453,496 A | 9/1995 | Caruthers et al. | |
| 5,484,596 A | 1/1996 | Hanna, Jr. et al. | |
| 5,629,158 A | 5/1997 | Uhlen | |
| 5,663,153 A | 9/1997 | Hutcherson et al. | |
| 5,723,335 A | 3/1998 | Hutcherson et al. | |
| 5,770,434 A | 6/1998 | Huse | |
| 5,824,812 A | 10/1998 | Nantz et al. | |
| 5,849,719 A | 12/1998 | Carson et al. | |
| 6,086,901 A | 7/2000 | O'Hagan et al. | |
| 6,174,872 B1 | 1/2001 | Carson et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,239,116 B1 | 5/2001 | Krieg et al. | |
| 6,306,405 B1 | 10/2001 | O'Hagan et al. | |
| 6,352,975 B1 | 3/2002 | Schreiner et al. | |
| 6,355,267 B1 | 3/2002 | Collins | |
| 6,458,370 B1 | 10/2002 | O'Hagan et al. | |
| 6,465,188 B1 | 10/2002 | Gold et al. | |
| 6,498,148 B1 | 12/2002 | Raz | |
| 6,514,948 B1 | 2/2003 | Raz et al. | |
| 6,534,062 B2 | 3/2003 | Raz et al. | |
| 6,544,518 B1 | 4/2003 | Friede et al. | |
| 6,552,006 B2 | 4/2003 | Raz et al. | |
| 6,558,670 B1 | 5/2003 | Friede et al. | |
| 6,559,129 B1 | 5/2003 | Kasid et al. | |
| 6,562,798 B1 | 5/2003 | Schwartz | |
| 6,589,940 B1 | 7/2003 | Raz et al. | |
| 6,610,661 B1 | 8/2003 | Carson et al. | |
| 6,613,751 B2 | 9/2003 | Raz et al. | |
| 6,737,006 B2 | 5/2004 | Grohman | |
| 6,855,492 B2 | 2/2005 | O'Hagan et al. | |
| 6,884,435 B1 | 4/2005 | O'Hagan et al. | |
| 6,893,821 B2 | 5/2005 | Raz et al. | |
| 7,129,222 B2 | 10/2006 | Van Nest et al. | |
| 7,157,437 B2 | 1/2007 | Van Nest | |
| 7,183,111 B2 | 2/2007 | Van Nest et al. | |
| 7,186,700 B2 | 3/2007 | Standring et al. | |
| 7,223,398 B1* | 5/2007 | Tuck et al. | 424/184.1 |
| 7,250,403 B2 | 7/2007 | Van Nest et al. | |
| 7,255,868 B2* | 8/2007 | Fearon et al. | 424/280.1 |
| 7,399,472 B2* | 7/2008 | Friede et al. | 424/184.1 |
| 7,625,872 B2* | 12/2009 | Fearon | 514/44 R |
| 7,628,990 B2* | 12/2009 | Tuck et al. | 424/184.1 |
| 7,745,606 B2* | 6/2010 | Dina et al. | 536/24.2 |
| 7,785,610 B2* | 8/2010 | Fearon et al. | 424/278.1 |
| 7,884,083 B2* | 2/2011 | Van Nest et al. | 514/44 R |
| 7,928,086 B2* | 4/2011 | Standring et al. | 514/49 |
| 7,935,351 B2* | 5/2011 | Klinman et al. | 424/198.1 |
| 7,935,675 B1* | 5/2011 | Krieg et al. | 514/44 R |
| 7,956,043 B2* | 6/2011 | Krieg et al. | 514/44 R |
| 7,959,934 B2* | 6/2011 | Klinman et al. | 424/278.1 |
| 7,960,356 B2* | 6/2011 | Klinman et al. | 514/44 R |
| 7,993,648 B2* | 8/2011 | Kedl et al. | 424/153.1 |
| 7,993,659 B2* | 8/2011 | Noelle et al. | 424/278.1 |
| 7,998,492 B2* | 8/2011 | Ahluwalia et al. | 424/278.1 |
| 8,003,115 B2* | 8/2011 | Fearon et al. | 424/280.1 |
| 8,008,266 B2* | 8/2011 | Krieg et al. | 514/44 R |
| 8,017,749 B2* | 9/2011 | Das Gupta et al. | 536/23.1 |
| 8,021,834 B2* | 9/2011 | O'Hagan et al. | 435/5 |
| 8,030,285 B2* | 10/2011 | Klinman et al. | 514/44 R |
| 8,034,802 B2* | 10/2011 | Averett | 514/183 |
| 8,043,622 B2* | 10/2011 | Klinman et al. | 424/184.1 |
| 2001/0046967 A1 | 11/2001 | Van Nest | |
| 2002/0055477 A1 | 5/2002 | Nest et al. | |
| 2003/0022852 A1 | 1/2003 | Nest et al. | |
| 2003/0059773 A1 | 3/2003 | Van Nest et al. | |
| 2003/0129251 A1 | 7/2003 | Van Nest et al. | |
| 2003/0133988 A1 | 7/2003 | Fearon et al. | |
| 2003/0175731 A1 | 9/2003 | Fearon et al. | |
| 2003/0199466 A1 | 10/2003 | Fearon et al. | |
| 2003/0216340 A1 | 11/2003 | Van Nest et al. | |
| 2005/0037403 A1 | 2/2005 | Krieg et al. | |
| 2010/0184834 A1* | 7/2010 | Dina et al. | 514/44 R |
| 2010/0291218 A1* | 11/2010 | Fearon et al. | 424/489 |
| 2011/0038896 A1* | 2/2011 | Van Nest et al. | 424/400 |
| 2011/0123561 A1* | 5/2011 | Barrat et al. | 424/193.1 |
| 2011/0180430 A1* | 7/2011 | Rappuoli et al. | 206/223 |

FOREIGN PATENT DOCUMENTS

| | | |
|---|---|---|
| EP | 0 468 520 A3 | 1/1992 |
| WO | WO-96/02555 A1 | 2/1996 |
| WO | WO-97/28259 A1 | 8/1997 |
| WO | WO-98/04740 A1 | 2/1998 |
| WO | WO-98/16247 A1 | 4/1998 |
| WO | WO-98/18810 A1 | 5/1998 |
| WO | WO-98/37919 A1 | 9/1998 |
| WO | WO-98/40100 A1 | 9/1998 |
| WO | WO-98/52581 A1 | 11/1998 |
| WO | WO-98/52962 A1 | 11/1998 |
| WO | WO-98/55495 A2 | 12/1998 |
| WO | WO-98/55495 A3 | 12/1998 |
| WO | WO-98/55609 A1 | 12/1998 |
| WO | WO-99/11275 A2 | 3/1999 |
| WO | WO-99/11275 A3 | 3/1999 |
| WO | WO-99/33488 A2 | 7/1999 |
| WO | WO-99/33488 A3 | 7/1999 |
| WO | WO-99/33868 A2 | 7/1999 |
| WO | WO-99/33868 A3 | 7/1999 |
| WO | WO-99/51259 A2 | 10/1999 |
| WO | WO-99/51259 A3 | 10/1999 |
| WO | WO-99/56755 A1 | 11/1999 |
| WO | WO-99/62923 A2 | 12/1999 |
| WO | WO-99/62923 A3 | 12/1999 |
| WO | WO-00/06588 A1 | 2/2000 |
| WO | WO-00/06588 B1 | 2/2000 |
| WO | WO-00/16804 A1 | 3/2000 |
| WO | WO-00/21556 A1 | 4/2000 |
| WO | WO-00/54803 A2 | 9/2000 |
| WO | WO-00/54803 A3 | 9/2000 |
| WO | WO-00/61161 A2 | 10/2000 |
| WO | WO-00/61161 A3 | 10/2000 |
| WO | WO-00/62800 A2 | 10/2000 |
| WO | WO-00/62800 A3 | 10/2000 |
| WO | WO-00/67023 A1 | 11/2000 |
| WO | WO-01/00231 A2 | 1/2001 |
| WO | WO-01/00231 A3 | 1/2001 |
| WO | WO-01/12223 A2 | 2/2001 |
| WO | WO-01/12223 A3 | 2/2001 |
| WO | WO-01/15726 A2 | 3/2001 |
| WO | WO-01/15726 A3 | 3/2001 |
| WO | WO-01/22972 A2 | 4/2001 |
| WO | WO-01/22972 A3 | 4/2001 |
| WO | WO-01/22990 A2 | 4/2001 |
| WO | WO-01/22990 A3 | 4/2001 |
| WO | WO-01/35991 A2 | 5/2001 |
| WO | WO-01/35991 A3 | 5/2001 |
| WO | WO-01/51500 A1 | 7/2001 |
| WO | WO-01/54720 A1 | 8/2001 |
| WO | WO-01/68077 A2 | 9/2001 |
| WO | WO-01/68077 A3 | 9/2001 |
| WO | WO-01/68078 A2 | 9/2001 |
| WO | WO-01/68078 A3 | 9/2001 |
| WO | WO-01/68103 A2 | 9/2001 |
| WO | WO-01/68103 A3 | 9/2001 |
| WO | WO-01/68116 A2 | 9/2001 |
| WO | WO-01/68116 A3 | 9/2001 |
| WO | WO-01/68117 A2 | 9/2001 |
| WO | WO-01/68117 A3 | 9/2001 |
| WO | WO-01/68143 A2 | 9/2001 |
| WO | WO-01/68143 A3 | 9/2001 |
| WO | WO-01/68144 A2 | 9/2001 |
| WO | WO-01/68144 A3 | 9/2001 |
| WO | WO-01/76642 A1 | 10/2001 |
| WO | WO-03/015816 A1 | 2/2003 |
| WO | WO 2004/058179 A2 * | 7/2004 |

| WO | WO 2010/138192 A2 * 12/2010 |
| WO | WO 2010/138193 A2 * 12/2010 |
| WO | WO 2010/138194 A2 * 12/2010 |

OTHER PUBLICATIONS

Krishnamachari et al, Advanced Drug Delivery Revs., 2009, 61/3:205-217.*
Wheeler et al, Allergology International, 2001, 50:295-301.*
Xie et al, Infection and Immunity, Feb. 2005, 73/2:828-833.*
Singh et al, Pharmaceutical Research, Oct. 2001, 18/10:1476-1479.*
Singh et al, Expert Rev. Vaccines, 2007, 6/5:797-808.*
Krieg, BioDrugs 1998, 5:341-346.*
Goldberg et al, Immunology Letters, 2000, 73:13-18.*
McCluskie et al, Molecular Med, 1999, 5/5:287-300.*
Krieg et al, Immunology Today, 2000, 21/10:521-526.*
Weiner, J. Leukocyte Biology, 2000, 68:456-463.*
Aderem, A. et al. (Dec. 22, 2000). "How do you see CG?" Cell 103:993-996.
Agrawal et al. (1986). "Efficient methods for attaching non-radioactive labels to the 5' ends of synthetic oligodeoxyribonucleotides," Nucleic Acids Res. 14:6227-6245.
Agrawal, S. et al. (Feb. 2000). "Antisense Therapeutics: is it as Simple as Complementary Base Recognition?," Molecular Med. Today 6:72-81.
Ahmeida, E.T.S. Ben, (1993). "Immunopotentiation of local and systemic humoral immune responses by ISCOMs, liposomes and FCA: role in protection against influenze A in mice," Vaccine 11(13):1302-1309.
Asanuma, H. et al., (1995) "Cross-protection against influenza virus infection in mice vaccined by combined nasal/subcutaneous administration" Vaccine 13:3-5.
Atherton et al. (1981). "Synthesis of a 21-residue fragment of human proinsulin by the polyamide solid phase method," Hoppe-Seylers Z. Physiol. Chem. 362:833-839.
Ballas et al. (1996). "Induction of NK activity in murine and human cells by CpG motifs in oligodeoxynucleotides and bacterial DNA," J.Immunol. 157:1840-1845.
Benoit et al. (1987). "Peptides. Strategies for antibody production and radioimmunoassays," Neuromethods 6:43-72.
Bhatt, R. et al. (1999) "Detection of nucleic acids by cycling probe technology on magnetic particles: high sensitivity and ease of separation," Nucleosides & Nucleotides 18(6&7):1297-1299.
Bischoff et al. (1987). "Introduction of 5'-terminal functional groups into synthetic oligonucleotides for selective immobilization," Analytical Biochemistry 164:336-344.
Blanks et al. (1988). "An oligodeoxynucleotide affinity column for the isolation of sequence specific DNA binding proteins," Nucleic Acids Res. 16:10283-10299.
Boujrad et al. (1993). "Inhibition of hormone-stimulated steroidogenesis in cultured Leydig tumor cells by a cholesterol-linked phosphorothioate oligodeoxynucleotide antisense to diazepam-binding inhibitor," Proc. Natl. Acad. Sci. USA 90:5728-5731.
Branda et al. (1993)."Immune stimulation by an antisense oligomer complementary to the rev gene of HIV-1," Biochem. Pharmacol. 45:2037-2043.
Branda et al. (1996). "Amplification of antibody production by phosphorothioate oligodeoxynucleotides," J. Lab. Clin. Med. 128:329-338.
Braun et al. (1988). "Immunogenic duplex nucleic acids are nuclease resistant," J. Immunol. 141:2084-2089.
Brazolot Millan et al. (1998) "CpG DNA can induce strong Th1 humoral and cell-mediated immune responses against hepatitis B surface antigen in young mice," Proc. Natl. Acad. Sci. USA 95:15553-15558.
Breiteneder et al. (1989). "The gene coding for the major birch pollen allergen Betvl is highly homologous to a pea disease resistance response gene," EMBO J. 8:1935-1938.
Broide et al. (1998). "Immunostimulatory DNA sequences inhibit IL-5, eosinophilic inflammation, and airway hyperresponsiveness in mice," J. Immunol. 161:7054-7062.

Broide et al. (1999). "DNA-based immunization for asthma," Int. Arch. Allergy Immunol. 118:453-456.
Busquets, M.A. et al. (Nov. 2003). "Peptides and Liposomes: From Biophysical to Immunogenic Studies," Current Drug Targets 4(8):633-642.
Carson et al. (1997). "Oligonucleotide adjuvants for T helper 1 (Th1)-specific vaccination," J. Exp. Med. 186:1621-1622.
Chace et al. (1997). "Bacterial DNA-induced NK cell IFN-γ-production is dependent on macrophage secretion of IL-12," Clin. Immunol. and Immunopathol. 84:185-193.
Chaturvedi et al. (1996). "Stabilization of triple-stranded oligonucleotide complexes: use of probes containing alternating phosphodiester and stereo-uniform cationic phosphoramidate linkages," Nucleic Acids Res. 24:2318-2323.
Chen et al. (1999). "Enhanced protection against a lethal influenza virus challenge by immunization with both hemagglutinin- and neuraminidase-expressing DNAs," Vaccine 17:653-659.
Chu et al. (1997). "CpG oligodeoxynucleotides act as adjuvants that switch on T helper 1 (Th1) immunity," J. Exp. Med. 186:1623-1631.
Chua et al. (1988). "Sequence analysis of cDNA coding for a major house dust mite allergen, Der p 1 homology with cysteine proteases," J. Exp. Med. 167:175-182.
Chua et al. (1990). "Expression of Dermatophagoides pteronyssinus allergen, Der p II, in Escherichia coli and the binding studies with human IgE," Int. Arch. Allergy Appl. Immunol. 91:124-129.
Connolly, Bernard A. (1985). "Chemical synthesis of oligonucleotides containing a free sulphydryl group and subsequent attachment of thiol specific probes," Nucleic Acids Res. 13:4485-4502.
Connolly, Bernard A. (1987). "The synthesis of oligonucleotides containing a primary amino group at the 5'-terminus," Nucleic Acids Res. 15:3131-3139.
Corey et al. (1987). "Generation of a hybrid sequence-specific single-stranded deoxyribonuclease," Science 238:1401-1403.
Cowdery et al. (1996). "Bacterial DNA induces NK cells to produce IFN-γ in vivo and increases the toxicity of lipopolysaccharides," J. Immunol. 156:4570-4575.
Crooke, S.T. (1998). "Basic Principals of Antisense Therapeutics," Chapter 1 In Antisense Research and Application, Crooke, S.T. ed., Springer-Verlag: Berlin, Germany, pp. 1-50.
De Martino et al. (1999). "Low IgG3 and high IgG4 subclass levels in children with advanced human immunodeficiency virus-type 1 infection and elevated IgE levels," Ann. Allergy Asthma Immunol. 83:160-164.
Du Bois, R.M. (Oct. 21, 1999). "Interferon Gamma-1b for the Treatment of Idiopathic Pulmonary Fibrosis," New England Journal of Medicine 341(17):1302-1304.
Elkins et al., (1999) "Bacterial DNA comprising CpG motifs stimulates lymphocyte-dependent protection of mice against lethal infection with intracellular bacteria" J. Immunol. 162:2291-2298.
Elsayed et al. (1991). "The structural requirements of epitopes with IgE binding capacity demonstrated by three major allergens from fish, egg and tree pollen," Scand. J. Clin. Lab. Invest. 51(Suppl. 204):17-31.
Fearon, K. et al. (2003). "A Minimal Human Immunostimulatory CpG Motif That Potently Induces IFN-γ and IFN-α production," Eur. J. Immunol. 33:2114-2122.
Fix, M. et al. (2002). "The Fluorosome™ Technique for Investigating Membrane On- and Off-loading of Drugs by β-CD and Sonicated SUV," FEBS Letters 516:109-112.
Fornadley, John (1998). "Allergy immunotherapy," Otolaryngol. Clin. North Am. 31:111-127.
Fritz et al. (1997). "Cationic Polystyrene Nanoparticles: Preparation and Characterization of a Model Drug Carrier System for Antisense Oligonucleotides," Journal of Colloid and Interface Science 195:272-288.
Gao et al., (1995). "Circularization of oligonucleotides by disulfide bridge formation," Nucleic Acids Res. 23(11):2025-2029.
Geoghegan et al. (1992). "Site-directed conjugation of nonpeptide groups to peptides and proteins via periodate oxidation of a 2-amino alcohol. Application to modification at N-terminal serine," Bioconjug. Chem. 3:138-146.

Godard et al. (1995) "Antisense effects of cholesterol-oligodeoxynucleotide conjugates associated with poly(alkylcyanoacrylate) nanoparticles" *Eur. J. Biochem.* 232:404-410.

Goodchild, John (1990). "Conjugates of oligonucleotides and modified oligonucleotides: A review of their synthesis and properties" *Bioconjug. Chem.* 1(3):165-187.

Govorkova et al. (1997). "Cross-protection of mice immunized with different influenza A (H2) strains and challenged with viruses of the same HA subtype," *Acta Virol.* 41:251-257.

Grabarek et al., "Zero-length crosslinking procedure with the use of active esters" (1990) *Anal. Biochem.* 185:131-135.

Gramzinski et al., "Immune response to a hepatitis B DNA vaccine in *aotus* monkeys: A comparison of vaccine formulation, route, and method of administration" (1998) *Mol. Med.* 4:109-118.

Granoff, Dan M. (1993). "Effect of immunity to the carrier protein on antibody responses to *Haemophilus influenzae* type b conjugate vaccines," *Vaccine* 11(1):S46-S51.

Gursel, I. et al. (2001). "Sterically Stabilized Cationic Liposomes Improve the Uptake and Immunostimulatory Activity of CpG Oligonucleotides," *J. Immunology* 167:3324-3328.

Haralambidis et al. (1990). "The preparation of polyamide-oligonucleotide probes containing multiple non-radioactive labels," *Nucleic Acids Res.* 18:501-505.

Haralambidis et al. (1990). "The synthesis of polyamide-oligonucleotide conjugate molecules," *Nucleic Acids Res.* 18:493-499.

Horner et al. (1998). "Rapid communication: Immunostimulatory DNA is a potent mucosal adjuvant," *Cell Immunol.* 190:77-82.

International Search Report mailed on Feb. 11, 2002 for PCT Application No. PCT/US01/07848 filed Mar. 12, 2001, three pages.

International Search Report mailed on Aug. 27, 2002 for PCT Application No. PCT/US01/25364 filed Aug. 13, 2001, four pages.

International Search Report mailed on Feb. 11, 2002 for PCT Application No. PCT/US01/07843 filed Mar. 12, 2001, three pages.

Jäger et al. (1988). "Oligonucleotide N-alkylphosphoramidates: Synthesis and binding to polynucleotides," *Biochem.* 27:7237-7246.

Jakob et al. (1998). "Activation of cutaneous dendrific cells by CpG-containing oligodeoxynucleotides: A role for dendritic cells in the augmentation of Th1 responses by immunostimulatory DNA," *J. Immunol.* 161:3042-3049.

Kandimalla, E.R. et al. (2001). "Effect of Chemical Modifications of Cytosine and Guanine in a CpG-motif of Oligonucleotides: Structure-Immunostimulatory Activity Relationships," *Bioorg. Med. Chem.* 9:807-813.

Kataoka et al. (1992). "Antitumor activity of synthetic oligonucleotides with sequences from cDNA encoding proteins of *Mycobacterium bovis* BCG," *Jpn. J. Cancer Res.* 83:244-247.

Kato, D. et al. (2003). "The Design of Polymer Microcarrier Surfaces for Enhanced Cell Growth," *Biomaterials* 24:4253-4264.

Kazzaz, J. et al. (2000). "Novel Anionic Microparticles are a Potent Adjuvant for the Induction of Cytotoxic T Lymphocytes Against Recombinant p55 gag From HIV-1," *J. Controlled Release* 67:347-356.

Kikuta, K. et al., (1990) Cross-protection against influenza B type virus infection by intranasal inoculation of the HA vaccines combined with cholera toxin B subunit *Vaccine* 8:595-599.

Kimura et al. (1994). "Binding of oligoguanylate to scavenger receptors is required for oligonucleotides to augment NK cell activity and induce IFN," *J. Biochem.* (Tokyo) 116:991-994.

Kline et al. (1997). "Immune redirection by CpG oligonucleotides conversion of a Th2 response to a Th1 response in a murine model of asthma," *J. Invest. Med.* 45(3):282A.

Klinman et al. (1996). "CpG motifs present in bacterial DNA rapidly induce lymphocytes to secrete interleukin 6, interleukin 12, and interferon γ," *Proc. Natl. Acad. Sci. USA* 93:2879-2883.

Klinman et al., (1997). "Contribution of CpG motifs to the immunogenicity of DNA vaccines," *J. Immunol.* 158:3635-3639.

Klinman, D.M. et al. (2004). "Use of CpG Oligodeoxynucleotides as Immune Adjuvants," *Immunological Reviews* 199:201-216.

Kodihalli et al., (1997). "Cross-protection among lethal H5N2 influenza viruses induced by DNA vaccine to the hemagglutinin,"*J. Virol.* 71(5):3391-3396.

Kofler, N. et al. (1996). "Preparation and Characterization of Poly-(D,L-lactide-co-glycolide) and Poly-(L-lactic acid) Microspheres with Entrapped Pneumotropic Bacterial Antigens.," *J. Immunological Methods* 192:25-35.

Kovarik et al. (1999). "CpG oligodeoxynucleotides can circumvent the Th2 polarization of neonatal responses to vaccines but may fail to fully redirect Th2 responses established by neonatal priming," *J. Immunol.* 162:1611-1617.

Kremsky et al. (1987). "Immobilization of DNA via oligonucleotides containing an aldehyde or carboxylic acid group at the 5' terminus," *Nucleic Acids Res.* 15:2891-2909.

Krieg et al. (1989). "A role for endogenous retroviral sequences in the regulation of lymphocyte activation," *J. Immunol.* 143:2448-2451.

Krieg et al. (1995). "CpG motifs in bacterial DNA trigger direct B-cell activation" *Nature* 374:546-549.

Krieg et al. (1996). "Oligodeoxynucleotide modifications determine the magnitude of B cell stimulation by CpG motifs," *Antisense & Nucleic Acid Drug Dev.* 6:133-139.

Krieg, Arthur M. (1996). "Lymphocyte activation by CpG dinucleotide motifs in prokaryotic DNA," *Trends in Microbiology* 4:73-77.

Krieg et al., (1998). "The role of CpG dinucleotides in DNA vaccines" *Trends Microbiol.* 6:23-27.

Krieg, Arthur M. (1998). "Leukocyte stimulation by oligodeoxynucleotides" Chapter 24 in *Applied Antisense Oligonucleotide Technology*. C.A. Stein et al. eds. Wiley-Liss, Inc.: pp. 431-448.

Krieg et al., "Sequence motifs in adenoviral DNA block immune activation by stimulatory CpG motifs" (1998) *Proc. Natl. Acad. Sci. USA* 95:12631-12636.

Krieg et al., "CpG DNA induces sustained IL-12 expression in vivo and resistance to *Listeria monocytogenes* challenge" (1998) *J. Immunol.* 161:2428-2434.

Krieg et al., (1999) "CpG DNA: a novel immunomodulator" *Trends Microbiol.* 7(2):64-65.

Krieg, A.M. (2002). "CpG motifs in Bacterial DNA and Their Immune Effects," *Annual Review Immunology* 20:709-760.

Latimer et al., "Specificity of monoclonal antibodies produced against phosphorothioate and ribo modified DNAs," (1995) *Mol. Immunol.* 32:1057-1064.

Lea et al. "Cloning and sequencing of cDNAs encoding the human sperm protein, Sp17" (1996) *Biochim. Biophys. Acta* 1307:263-266.

Lefeber, D.J. et al. (Dec. 2003). "Th1-directing Adjuvants Increase the Immunogenicity of Oligosaccharide-protein Conjugate Vaccines Related to *Streptococcus pneumoniae* Type 3," *Infection and Immunity* 71(12):6915-6920.

Leclerc et al., (1997) "The preferential induction of a TH1 immune response by DNA-based immunization is mediated by the immunostimulatory effect of plasmid DNA" *Cell. Immunol.* 179:97-106.

Lewis et al. (1998). "Development of a sustained-release biodegradable polymer delivery system for site-specific delivery of oligonucleotides: characterization of P(LA-GA) copolymer microspheres in vitro," *Journal of Drug Targeting* 5(4):291-302.

Li, Q.T. et al. (1993). "Effect of Cholesteryl Ester on the Distribution of Fluorescent Cholesterol Analogues in Triacylglycerol-rich Emulsions," *Biochimica et Biophysica Acta* 1166(2/3):145-153.

Liang, Hua et al. (1996). "Activation of human B cells by phosphoroghioate oligodeoxynucleotides," *J. Clin. Invest.* 98(5):1119-1129.

Lipford et al., "CpG-containing synthetic oligonucleotides promote B and cytotoxic T cell responses to protein antigen: a new class of vaccine adjuvants" (1997) *Eur. J. Immunol.* 27:2340-2344.

Lipford et al., "Immunostimulatory DNA: sequence-dependent production of potentially harmful or useful cytokines" (1997) *Eur. J. Immunol.* 27:3420-3426.

Liu et al., "Immunostimulatory CpG oligodeoxynucleotides enhance the immune response to vaccine strategies involving granulocyte-macrophage colony-stimulating factor" (1998) *Blood* 92:3730-3736.

MacFarlane et al., "Unmethylated CpG-containing oligodeoxynucleotides inhibit apoptosis in WEHI 231 B lymphocytes induced by several agents: evidence for blockade of apoptosis at a distal signalling step" (1997) *Immunology* 91:586-593.

Malley, Arthur, "The immune response of offspring mice from mothers immunized during pregnancy with protein antigens" (1989) *J. Reprod. Immunol.* 16:173-186.
Maloy, K.J. et al. (1994). "Induction of Mucosal and Systemic Immune Responses by Immunization with Ovalbumin Entrapped in Poly(lactide-co-glycolide) Microparticles," *Immunology* 81:661-667.
Manzel et al., (1999) "Lack of immune stimulation by immobilized CpG-oligodeoxynucleotide," *Antisense Nucl. Acid Drug Dev.* 9:459-464.
Martin-Orozco et al., "Enhancement of antigen-presenting cell surface molecules involved in cognate interactions by immunostimulatory DNA sequences," (1999) *Intnl Immunol.* 11(7):1111-1118.
Mbawuike et al., "Influenza: A subtype cross-protection after immunization of outbred mice with a purified chimeric $NS_1/HA_2$ influenza virus protein," (1994) *Vaccine* 12(14):1340-1348.
McCluskie et al., "Cutting edge: CpG DNA is a potent enhancer of systemic and mucosal immune responses against hepatitis B surface antigen with intranasal administration to mice," (1998) *J. Immunol.* 161(9):4463-4466.
Miller et al., "Syntheses and properties of adenine and thymine nucleoside alkyl phosphotriesters, the neutral analogs of dinucleoside monophosphates," (1971) *JACS* 93:6657-6665.
Mitragotri et al., "Ultrasound-mediated transdermal protein delivery," (1995) *Science* 269:850-853.
Mojcik et al., "Administration of a phosphorothioate oligonucleotide antisense to murine endogenous retroviral MCF *env* causes immune effects in vivo in a sequence-specific manner," (1993) *Clin. Immuno. and Immunopathol.* 67:130-136.
Moldoveanu et al. (1998). "CpG DNA, a novel immune enhancer for systemic and mucosal immunization with influenza virus," *Vaccine* 16:1216-1224.
Nellore, R.V. et al. (Sep.-Oct. 1992). "Evaluation of Biodegradable Microspheres as Vaccine Adjuvant for Hepatitis B Surface Antigen," *J. Parenteral Science and Technology* 46(5):176-180.
Nelson et al. (1989) "A new and versatile reagent for incorporating multiple primary aliphatic amines into synthetic oligonucleotides" *Nucleic Acids Res.* 17(18):7179-7186.
Nelson et al., "N3'→P5' oligodeoxyribonucleotide phosphoramidates: A new method of synthesis based on a phosphoramidite amino-exchange reaction," (1997) *J. Org. Chem.* 62:7278-7287.
O'Hagan, D.T. et al. (2000). "Microparticles in MF59, a Potent Adjuvant Combination for a Recombinant Protein Vaccine Against HIV-1," *Vaccine* 18:1793-1801.
O'Hagan, D.T. et al. (2001). "Recent Developments in Adjuvants for Vaccines Against Infectious Diseases," *Biomolecular Engineering* 18:69-85.
O'Hagan, D.T. et al. (2002). "Synergistic Adjuvant Activity of Immunostimulatory DNA and Oil/water Emulsions for Immunization with HIV p55 gag Antigen," *Vaccine* 20:3389-3398.
O'Shannessy et al., "Specific conjugation reactions of the oligosaccharide moieties of immunoglobulins" (1985) *J. Applied Biochem.* 7:347-355.
Peracchi, A. (2004). "Prospects for Antiviral Ribozymes and Deoxyribozymes," *Rev. Med. Virol.* 14:47-64.
Pertmer et al., "Influenza virus nucleoprotein-specific immunoglobulin G subclass and cytokine responses elicited by DNA vaccination are dependent on the route of vector DNA delivery" (1996) *J. Virol.* 70:6119-6125.
Peyrottes et al., "Oligodeoxynucleoside phosphoramidates (P-$NH_2$): synthesis and thermal stability of duplexes with DNA and RNA targets" (1996) *Nucleic Acids Res.* 24:1841-1848.
Pisetsky et al., "Immunological properties of bacterial DNA" DNA vaccines: A new era in vaccinology (1995) *Ann. N.Y. Acad. Sci.*, 772:152-163.
Pisetsky et al., "Stimulation of murine lymphocyte proliferation by a phosphorothioate oligonucleotide with antisense activity for herpes simplex virus" (1994) *Life Sci.* 54:101-107.
Pisetsky, David S., "Immune activation by bacterial DNA: A new genetic code" (1996b) *Immunity* 5:303-310.
Pisetsky, David S., "The immunologic properties of DNA" (1996a) *J. Immunol.* 156:421-423.

Plenat, F. (Jun. 1996). "Animal Models of Antisense Oligonucleotides: Lessons for use in Humans," *Molecular Medicine Today* 2(6):250-257.
Ponchel, G. et al. (1998). "Specific and Non-specific Bioadhesive Particulate Systems for Oral Delivery to the Gastrointestinal Tract," *Advanced Drug Delivery Reviews* 34:191-219.
Rafnar et al., "Cloning of *Amb a I* (antigen E), the major allergen family of short ragweed pollen" (1991) *J. Biol. Chem.* 266:1229-1236.
Raz et al., "Intradermal gene immunization: The possible role of DNA uptake in the induction of cellular immunity to viruses" (1994) *Proc. Natl. Acad. Sci. USA* 91:9519-9523.
Raz et al., "Preferential induction of a $Th_1$ immune response and inhibition of specific IgE antibody formation by plasmid DNA immunization" (1996) *Proc. Natl. Acad. Sci. USA* 93:5141-5145.
Redford et al., "Cyclosporin A enhances IL-12 production by CpG motifs in bacterial DNA and synthetic oligodeoxynucleotides" (1998) *J. Immunol.* 161:3930-3935.
Rogers et al., "Recombinant *Fel d* I: Expression, purification, IgE binding and reaction with cat-allergic human T cells" (1993) *Mol. Immunol.* 30:559-568.
Roget et al., "Synthesis and use of labelled nucleoside phosphoramidite building blocks bearing a reporter group: biotinyl, dinitrophenyl, pyrenyl and dansyl" (1989) *Nucleic Acids Res.* 17:7643-7651.
Romagnani, S. (2000) T-cell subsets (Th1 versus Th2) *Ann. Allergy Asthma Immunol.* 85:9-18.
Roman et al., "Immunostimulatory DNA sequences function as T helper-1-promoting adjuvants" (1997) *Nature Medicine* 3(8):849-854.
Ruth, Jerry L., "Oligodeoxynucleotides with reporter groups attached to the base" (1991) *Oligonucleotides and Analogues: A Practical Approach*, Eckstein, ed., IRL Press, pp. 255-282.
Ryan, E.J. et al. (Aug. 2001). "Immunomodulators and Delivery Systems for Vaccination by Mucosal Routes," *Trends in Biotechnology* 19(8):293-304.
Sato et al., "Immunostimulatory DNA sequences necessary for effective intradermal gene immunization" (1996) *Science* 273:352-354.
Schacht et al., (1996) "Biomedical applications of degradable polyphosphazenes" *Biotechnol. Bioeng.* 52:102-108.
Scherle et al., "Differential ability of B cells specific for external vs. internal influenza virus proteins to respond to help from influenza virus-specific T-cell clones in vivo" (1988) *Proc. Natl. Acad. Sci. USA* 85:4446-4450.
Scherle et al., "Functional analysis of influenza specific helper T cell clones in vivo" (1986) *J. Exp. Med.* 164:1114-1128.
Schultz et al., "Oligo-2'-fluoro-2'-deoxynucleotide N3'→P5' phosphoramidates: synthesis and properties" (1996) *Nucleic Acids Res.* 24:2966-2973.
Schwab et al. (1994). *Proc. Natl. Acad. Sci. USA* 91:10460-10464.
Schwartz et al., "CpG motifs in bacterial DNA cause inflammation in the lower respiratory tract" (1997) *J. Clin. Invest.* 100:68-73.
Shimada et al., "In vivo augmentation of natural killer cell activity with a deoxyribonucleic acid fraction of BCG" (1986) *Jpn. J. Cancer Res.* 77:808-816.
Singh, M. et al. (Nov. 1999). "Advances in Vaccine Adjuvants," *Nature Biotechnology* 17:1075-1081.
Singh, M. et al. (Jan. 18, 2000). "Cationic Microparticles: A Potent Delivery System for DNA Vaccines," *PNAS* 97(2):811-816.
Sinha et al., "Oligonucleotides with reporter groups attached to the 5'-terminus" (1991) *Oligonucleotide Analogues: A Practical Approach*, Eckstein, ed., IRL Press, pp. 185-210.
Sonehara et al., "Hexamer palindromic oligonucleotides with 5'-CG-3' motif(s) induce production of interferon" (1996) *J. Interferon and Cytokine Res.* 16:799-803.
Sparwasser et al., "Macrophages sense pathogens via DNA motifs: induction of tumor necrosis factor-α-mediated shock" (1997) *Eur. J. Immunol.* 27:1671-1679.
Spiegelberg et al., "Inhibition of allergic inflammation in the lung by plasmid DNA allergen immunization" (1999) *Pediatric Pulmonology* Suppl. 18:118-121.

Spiegelberg et al., "Inhibition of IgE formation and allergic inflammation by allergen gene immunization and by CpG motif immunostimulatory oligodeoxynucleotides" (1998) *Allergy* 53:93-97.

Stacey et al., "Macrophages ingest and are activated by bacterial DNA" (1996) *J. Immunol.* 157:2116-2122.

Staros et al., "Enhancement by N-hydroxysulfosuccinimide of water-soluble carbodiimide-mediated coupling reactions" (1986) *Anal. Biochem.* 156:220-222.

Stayton, P.S. et al. (2000). "Molecular Engineering of Proteins and Polymers for Targeting and Intracellular Delivery of Therapeutics," *J. Controlled Release* 65:203-220.

Stein et al., "Chapter 11: Non-antisense effects of oligodeoxynucleotides" (1997) *Antisense Technology*, C. Lichtenstein and W. Nellen, eds., IRL Press, pp. 241-264.

Stirchak et al., "Uncharged stereoregular nucleic acid analogs: 2. Morpholino nucleoside oligomers with carbamate internucleoside linkages" (1989) *Nucleic Acids Res.* 17:6129-6141.

Tamura et al., "Formulation of inactivated influenza vaccines for providing effective cross-protection by intranasal vaccination in mice," (1994) *Vaccine* 12:310-316.

Tamura et al., "Superior cross-protective effect of nasal vaccination to subcutaneous inoculation with influenza hemagglutinin vaccine," (1992) *Eur. J. Immunol.* 22:477-481.

Tokunaga et al., "Synthetic oligonucleotides with particular base sequences from the cDNA encoding proteins of *Mycobacterium bovis* BCG induce interferons and activate natural killer cells," (1992) *Microbiol. Immunol.* 36:55-66.

Tung et al., "Preparation of oligonucleotide-peptide conjugates," (1991) *Bioconjug. Chem.* 2:464-465.

Uhlmann, E. et al. (2003). "Recent Advances in the Development of Immunostimulatory Oligonucleotides," *Current Opinion in Drug Discovery and Development* 6(2):204-217.

Van Uden, J. et al. (Nov. 1999). "Immunostimulatory DNA and Applications to Allergic Disease," *Journal of Allergy and Clinical Immunology* 104(5):902-910.

Verthelvi, D. et al. (Feb. 15, 2001). "Humen Peripheral Blood Cells Differentially Recognize and Respond to Two Distinct CpG Motifs," *J. Immunol.* 166(4):2372-2377.

Wang et al., "Circular RNA oligonucleotides. Synthesis, nucleic acid binding properties, and a comparison with circular DNAs," (1994) *Nucleic Acids Res.* 22:2326-2333.

Warner et al., "Laboratory methods. Construction and evaluation of an instrument for the automated synthesis of oligodeoxyribonucleotides," (1984) *DNA* 3:401-411.

Weeratna et al. (1998) "Brief Communication: Reduction of antigen expression from DNA vaccines by coadministered oligodeoxynucleotides," *Antisense & Nucleic Acid Drug Development* 8:351-356.

Weeratna, R.D. et al. (2000). "CpG DNA Induces Stronger Immune Responses with less Toxicity than Other Adjuvants," *Vaccine* 18:1755-1762.

Weiner et al., "Immunostimulatory oligodeoxynucleotides containing the CpG motif are effective as immune adjuvants in tumor antigen immunization," (1997) *Proc. Natl. Acad. Sci. USA* 94:10833-10837.

Widhe, M. et al. (1998). "IgG subclasses in lyme borreliosis: A study of specific IgG subclass distribution in an interferon-γ-predominated disease," *Scand. J. Immunol.* 47:575-581.

Wooldridge et al., "Immunostimulatory oligodeoxynucleotides containing CpG motifs enhance the efficacy of monoclonal antibody therapy of lymphoma" (1997) *Blood* 89:2994-2998.

Yanagawa et al., "Analysis of superhelical structures of nucleic acid-lipid conjugates by image processing" (1988) *Nucleic Acids Symp. Series* 19:189-192.

Yamamoto et al., "Unique palindromic sequences in synthetic oligonucleotides are required to induce INF and augment INF-mediated natural killer activity" (1992) *J. Immunol.* 148:4072-4076.

Yamamoto et al. (1994) "Ability of oligonucleotides with certain palindromes to induce interferon production and augment natural killer cell activity is associated with their base length" *Antisense Research and Development* 4:119-122.

Yamamoto et al., "Synthetic oligonucleotides with certain palindromes stimulate interferon production of human peripheral blood lymphocytes in vitro" (1994) *Jpn. J. Cancer Res.* 85:775-779.

Yi et al. (1996) "IFN-γ promotes IL-6 and IgM secretion in response to CpG motifs in bacterial DNA and oligonucleotides" *J. Immunol.* 156:558-564.

Yi et al., "CpG DNA rescue from anti-IgM-induced WEHI-231 B lymphoma apoptosis via modulation of IκBα and Iκb/β and sustained activation of nuclear factor-κB/c-Rel" (1998) *J. Immunol.* 160:1240-1245.

Yi et al., "CpG motifs in bacterial DNA activate leukocytes through the pH-dependent generation of reactive oxygen species" (1998) *J. Immunol.* 160:4755-4761.

Yi et al., "CpG oligodeoxynucleotides rescue mature spleen B cells from spontaneous apoptosis and promote cell cycle entry" (1998) *J. Immunol.* 160:5898-5906.

Yi et al., "Cutting edge: Rapid induction of mitogen-activated protein kinases by immune stimulatory CpG DNA" (1998) *J. Immunol.* 161:4493-4497.

Zhao et al., "Effect of different chemically modified oligodeoxynucleotides on immune stimulation" (1996) *Biochem. Pharmacol.* 51:173-182.

Zimmermann et al., "Cutting edge: CpG oligodeoxynucleotides trigger protective and curative Th1 responses in lethal murine leishmaniasis" (1998) J. Immunol. 3627-3630.

Zon, Gerald, "Oligonucleoside phosphorothioates" Protocols for Oligonucleotides and Analogs, Chapter 8 in *Methods in Molecular Biology*, vol. 20 (1993) pp. 165-189.

Zuckermann et al., "Efficient methods for attachment of thiol specific probes to the 3'-ends of synthetic oligodeoxyribonucleotides" (1987) *Nucleic Acids Res.* 15:5305-5321.

Barr, I.G. et al. (1998). "ISCOMs and other Saponin Based Adjuvants," *Advanced Drug Delivery Reviews* 32:247-271.

Dow, S.W. et al. (1999). "Lipid-DNA Complexes Induce Potent Activation of Innate Immune Responses and Antitumor Activity when Administered Intravenously," *J. Immunology* 163:1552-1561.

Freimark, B.D. et al. (1998). "Cationic Lipids Enhance Cytokine and Cell Influx Levels in the Lung Following Administration of Plasmid: Cationic Lipid Complexes," *J. of Immunology* 160:4580-4586.

He, Q. et al. (Nov. 2000). "Calcium Phosphate Nanoparticle Adjuvant," *Clinical and Diagnostic Laboratory Immunology* 7(6):899-903.

Kreuter, J. (1996). "Nanoparticles and Microparticles for Drug and Vaccine Delivery," *J. Anat.* 189:503-505.

Mikayama, T. et al. (Nov. 1993). "Molecular Cloning and Functional Expression of a cDNA Encoding Glycosylation-inhibiting Factor," *Proc. Natl. Acad. Sci. USA* 90:10056-10060.

Rochlitz, C.F. (2001). "Gene Therapy of Cancer," *Swiss Medicine Weekly* 131:4-9.

Rudinger, J. (Jun. 1976). "Characteristics of the Amino Acids as Components of a Peptide Hormone Sequence," *Peptide Hormones* pp. 5-7.

Sjölander, A. et al. (1998). "Uptake and Adjuvant Activity of Orally Delivered Saponin and ISCOM™ Vaccines," *Advanced Drug Delivery Review* 34:321-338.

Tan, Y. et al. (Sep. 1, 1999). "The Inhibitory Role of CpG Immunostimulatory Motifs in Cationic Lipid Vector-Mediated Transgene Exprssion in Vivo," *Human Gene Therapy* 10:2153-2161.

U.S. Appl. No. 60/188,303, filed Mar. 10, 2000, for Van Nest et al.

Verma, I.M. et al. (Sep. 18, 1997). "Gene Therapy—Promises, Problems and Prospects," *Nature* 389(6648):239-242.

Vile, R.G. et al. (2000). "Cancer Gene Therapy: Hard Lessons and New Courses," *Gene Therapy* 7:2-8.

* cited by examiner

BIODEGRADABLE IMMUNOMODULATORY FORMULATIONS AND METHODS FOR USE THEREOF

CROSS-REFERENCE TO RELATED APPLICATIONS

This application is a divisional of U.S. application Ser. No. 09/927,422 filed Aug. 10, 2001, now U.S. Pat. No. 7,250,403, which is a continuation-in-part of U.S. application Ser. No. 09/802,359, filed Mar. 9, 2001, now abandoned, which in turn claims the priority benefit of U.S. Provisional application 60/188,303, filed Mar. 10, 2000, each of which is hereby incorporated herein by reference in their entirety.

TECHNICAL FIELD

The present invention relates to immunomodulatory compositions comprising an immunostimulatory oligonucleotide sequence (ISS) and methods of use thereof. In particular, the invention relates to immunomodulatory compositions comprising an ISS bound to a biodegradable microparticle. It also relates to the administration of the polynucleotide/microcarrier complex to modulate at least one immune response.

BACKGROUND ART

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9-18.

The Th1 subset may be particularly suited to respond to viral infections, intracellular pathogens, and tumor cells because it secretes IL-2 and IFN-$\gamma$, which activate CTLs. The Th2 subset may be more suited to respond to free-living bacteria and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences or "ISS," induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849-854. For example, mice injected intradermally with *Escherichia coli* (*E. coli*) $\beta$-galactosidase ($\beta$-Gal) in saline or in the adjuvant alum responded by producing specific IgG1 and IgE antibodies, and CD4$^+$ cells that secreted IL-4 and IL-5, but not IFN-$\gamma$, demonstrating that the T cells were predominantly of the Th2 subset. However, mice injected intradermally (or with a tyne skin scratch applicator) with plasmid DNA (in saline) encoding $\beta$-Gal and containing an ISS responded by producing IgG2a antibodies and CD4$^+$ cells that secreted IFN-$\gamma$, but not IL-4 and IL-5, demonstrating that the T cells were predominantly of the Th1 subset. Moreover, specific IgE production by the plasmid DNA-injected mice was reduced 66-75%. Raz et al. (1996) *Proc. Natl. Acad. Sci. USA* 93:5141-5145. In general, the response to naked DNA immunization is characterized by production of IL-2, TNF$\alpha$ and IFN-$\gamma$ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

ISS-containing oligonucleotides bound to microparticles (SEPHAROSE® beads) have previously been shown to have immunostimulatory activity in vitro (Liang et al., (1996), *J. Clin. Invest.* 98:1119-1129). However, recent results show that ISS-containing oligonucleotides bound to gold, latex and magnetic particles are not active in stimulating proliferation of 7TD1 cells, which proliferate in response to ISS-containing oligonucleotides (Manzel et al., (1999), *Antisense Nucl. Acid Drug Dev.* 9:459-464).

Other references describing ISS include: Krieg et al. (1989) *J. Immunol.* 143:2448-2451; Tokunaga et al. (1992) *Microbiol. Immunol.* 36:55-66; Kataoka et al. (1992) *Jpn. J. Cancer Res.* 83:244-247; Yamamoto et al. (1992) *J. Immunol.* 148:4072-4076; Mojcik et al. (1993) *Clin. Immuno. and Immunopathol.* 67:130-136; Branda et al. (1993) *Biochem. Pharmacol.* 45:2037-2043; Pisetsky et al. (1994) *Life Sci.* 54(2):101-107; Yamamoto et al. (1994a) *Antisense Research* and Development. 4:119-122; Yamamoto et al. (1994b) Jpn. J. Cancer Res. 85:775-779; Raz et al. (1994) Proc. Natl. Acad. Sci. USA 91:9519-9523; Kimura et al. (1994) J. Biochem. (Tokyo) 116:991-994; Krieg et al. (1995) Nature 374: 546-549; Pisetsky et al. (1995) Ann. N.Y. Acad. Sci. 772:152-163; Pisetsky (1996a) J. Immunol. 156:421-423; Pisetsky (1996b) Immunity 5:303-310; Zhao et al. (1996) Biochem. Pharmacol. 51:173-182; Yi et al. (1996) J. Immunol. 156: 558-564; Krieg (1996) Trends Microbiol. 4(2):73-76; Krieg et al. (1996) Antisense Nucleic Acid Drug Dev. 6:133-139; Klinman et al. (1996) Proc. Natl. Acad. Sci. USA. 93:2879-2883; Raz et al. (1996); Sato et al. (1996) Science 273:352-354; Stacey et al. (1996) J. Immunol. 157:2116-2122; Ballas et al. (1996) J. Immunol. 157:1840-1845; Branda et al. (1996) J. Lab. Clin. Med. 128:329-338; Sonehara et al. (1996) J. Interferon and Cytokine Res. 16:799-803; Klinman et al. (1997) J. Immunol. 158:3635-3639; Sparwasser et al. (1997) Eur. J. Immunol. 27:1671-1679; Roman et al. (1997); Carson et al. (1997) J. Exp. Med. 186:1621-1622; Chace et al. (1997) Clin. Immunol. and Immunopathol. 84:185-193; Chu et al. (1997) J. Exp. Med. 186:1623-1631; Lipford et al. (1997a) Eur. J. Immunol. 27:2340-2344; Lipford et al. (1997b) Eur. J. Immunol. 27:3420-3426; Weiner et al. (1997) Proc. Natl. Acad. Sci. USA 94:10833-10837; Macfarlane et al. (1997) Immunology 91:586-593; Schwartz et al. (1997) J. Clin. Invest. 100:68-73; Stein et al. (1997) Antisense Technology, Ch. 11 pp. 241-264, C. Lichtenstein and W. Nellen, Eds., IRL Press; Wooldridge et al. (1997) Blood 89:2994-2998; Leclerc et al. (1997) Cell. Immunol. 179:97-106; Kline et al. (1997) J. Invest. Med. 45(3):282A; Yi et al. (1998a) J. Immunol. 160: 1240-1245; Yi et al. (1998b) J. Immunol. 160:4755-4761; Yi et al. (1998c) J. Immunol. 160:5898-5906; Yi et al. (1998d) J. Immunol. 161:4493-4497; Krieg (1998) Applied Antisense Oligonucleotide Technology Ch. 24, pp. 431-448, C. A. Stein and A. M. Krieg, Eds., Wiley-Liss, Inc.; Krieg et al. (1998a) Trends Microbiol. 6:23-27; Krieg et al. (1998b) J. Immunol. 161:2428-2434; Krieg et al. (1998c) Proc. Natl. Acad. Sci. USA 95:12631-12636; Spiegelberg et al. (1998) Allergy 53(45S):93-97; Horner et al. (1998) Cell Immunol. 190:77-82; Jakob et al. (1998) J. Immunol. 161:3042-3049; Redford et al. (1998) J. Immunol. 161:3930-3935; Weeratna et al. (1998) Antisense & Nucleic Acid Drug Development 8:351-356; McCluskie et al. (1998) J. Immunol. 161(9):4463-4466; Gramzinski et al. (1998) Mol. Med. 4:109-118; Liu et al. (1998) Blood 92:3730-3736; Moldoveanu et al. (1998) Vaccine 16: 1216-1224; Brazolot Milan et al. (1998) Proc. Natl. Acad. Sci. USA 95:15553-15558; Briode et al. (1998) J. Immunol. 161:7054-7062; Briode et al. (1999) Int. Arch. Allergy Immunol. 118:453-456; Kovarik et al. (1999) J. Immunol. 162:1611-1617; Spiegelberg et al. (1999) Pediatr. Pulmonol. Suppl. 18:118-121; Martin-Orozco et al. (1999) Int. Immunol. 11:1111-1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) J. Immunol. 162:2291-2298, WO 98/52962, WO 99/33488, WO 99/33868, WO 99/51259 and WO 99/62923. See also Zimmermann et al. (1998) J. Immunol. 160:3627-3630; Krieg (1999) Trends Microbiol. 7:64-65; U.S. Pat. Nos. 5,663,153, 5,723,335, 5,849,719 and 6,174,872. See also WO 99/56755, WO 00/06588, WO 00/16804; WO 00/21556; WO 00/67023 and WO 01/12223. See also Verthelyi et al. (2001) J. Immunol. 166:2372-2377; WO 00/54803; WO 00/61161; WO 00/54803; WO 01/15726; WO 01/22972; WO 01/22990; WO 01/35991; WO 01/51500; WO 01/54720; U.S. Pat. Nos. 6,194,388, 6,207,646, 6,214,806, 6,239,116.

Additionally, Godard et al. (1995) Eur. J. Biochem. 232: 404-410, discloses cholesterol-modified antisense oligonucleotides bound to poly(isohexylcyanoacrylate) nanoparticles.

All patents, patent applications, and publications cited herein are hereby incorporated by reference in their entirety.

DISCLOSURE OF THE INVENTION

The invention relates to new compositions and methods for modulating immune responses in individuals, particularly human individuals.

In one aspect, the invention relates to compositions which comprise immunomodulatory polynucleotide/microcarrier (IMP/MC) complexes. An IMP/MC complex comprises a polynucleotide comprising an immunostimulatory sequence (IMP) linked to a filterable, insoluble, biodegradable microcarrier (MC). The IMP may be covalently or non-covalently linked to the microcarrier in the complex, and the IMP may be modified to facilitate complex formation. Microcarriers used in IMP/MC complexes are typically solid phase microcarriers, although biodegradable liquid phase microcarriers (e.g., an oil in water emulsion comprising a biodegradable polymer or oil) are also contemplated. Microcarriers are generally less than about 150, 120 or 100 µm, more commonly less than about 50-60 µm in size, and may be about 10 nm to about 10 µm or about 25 nm to 5 µm in size. In certain embodiments, the compositions of the invention comprise an IMP/MC complex and a pharmaceutically acceptable excipient. In certain embodiments, the compositions of the invention comprise an antigen-free IMP/MC complex, i.e., an IMP/MC complex not linked to an antigen (either directly or indirectly). In certain embodiments, the IMP/MC complex further comprises an antigen.

In another aspect, the invention relates to methods of modulating an immune response in an individual, comprising administering to an individual an IMP/MC complex in an amount sufficient to modulate an immune response in said individual. Immunomodulation according to the methods of the invention may be practiced on individuals including those suffering from a disorder associated with a Th2-type immune response (e.g., allergies or allergy-induced asthma), individuals receiving vaccines such as therapeutic vaccines (e.g., vaccines comprising an allergy epitope, a mycobacterial epitope, or a tumor associated epitope) or prophylactic vaccines, individuals with cancer, individuals having an infectious disease and individuals at risk of exposure to an infectious agent.

In a further aspect, the invention relates to methods of increasing interferon-gamma (IFN-$\gamma$) in an individual, comprising administering an effective amount of an IMP/MC complex to the individual. Administration of an IMP/MC complex in accordance with the invention increases IFN-$\gamma$ in the individual. Suitable subjects for these methods include those individuals having idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-$\gamma$.

In another aspect, the invention relates to methods of increasing IFN-$\alpha$ in an individual, comprising administering an effective amount of an IMP/MC complex to the individual. Administration of an IMP/MC complex in accordance with the invention increases IFN-$\alpha$ levels in the individual. Suitable subjects for these methods include those individuals having disorders which respond to the administration of IFN-$\alpha$, including viral infections and cancer.

In another aspect, the invention relates to methods of ameliorating one or more symptoms of an infectious disease, comprising administering an effective amount of an IMP/MC complex to an individual having an infectious disease. Administration of an IMP/MC complex in accordance with the invention ameliorates one or more symptoms of the infectious disease. The infectious diseases which may be treated in accordance with the invention include infectious diseases caused by a cellular pathogen (e.g., a mycobacterial disease, malaria, leishmaniasis, toxoplasmosis, schistosomiasis or clonorchiasis), and may include or exclude viral diseases.

The invention further relates to kits for carrying out the methods of the invention. The kits of the invention comprise a container comprising an IMP/MC complex (or as described herein, materials for production of IMP/MC complexes) and optionally include instructions for use of IMP/MC complex in immunomodulation of an individual, for example when the individual suffers from a disorder associated with a Th2-type immune response (e.g., allergies or allergy-induced asthma), is receiving vaccines such as therapeutic vaccines (e.g., vaccines comprising an allergy epitope, a mycobacterial epitope, or a tumor associated epitope) or prophylactic vaccines, suffers from cancer, suffers from an infectious disease or is at risk of exposure to an infectious agent.

The polynucleotide of the IMP/MC complexes of the invention comprises the sequence 5'-CG-3'. In certain embodiments, the polynucleotide of the IMP/MC complex comprises the sequence 5'-TCG-3'. In certain embodiments, the polynucleotide of the IMP/MC complex comprises the sequence 5'-CG-3' and further comprises the sequence 5'-TCG-3'. In certain embodiments, the polynucleotide of the IMP/MC complex is 7 nucleotides in length.

MODES OF PRACTICING THE INVENTION

We have discovered new compositions and methods for modulating immune responses in individuals, including and particularly humans. The compositions of the invention comprise an immunomodulatory polynucleotide (IMP) complexed with a biodegradable microcarrier (MC). We have found that immunomodulatory polynucleotides combined with nanometer-scale microcarriers (50 and 200 nm diameter beads) efficiently modulate immune cells, including human cells. IMPs combined with small microcarriers (approximately 1 to 4.5 μm, less than 2.0 μm or about 1.5 μm diameter) also immunomodulated human cells. Our discovery is of particular interest because human cells, as is known in the art, can be more resistant to immunomodulation by IMPs than cells from commonly used laboratory animals, such as mice.

We found that IMP/MC complexes were more effective at lower doses than free IMP alone in immunomodulation. In human cells, IMP/MC complexes were more active than free IMP in inducing IFN-γ and IFN-α.

The IMP/MC complexes may include or exclude an antigen. In some embodiments, the invention provides compositions comprising antigen-free IMP/MC complexes, i.e., IMP/MC complexes not linked to an antigen (directly or indirectly). In other embodiments, the invention provides compositions comprising IMP/MC complexes mixed with one or more antigens. In other embodiments, the invention provides compositions comprising IMP/MC complexes linked to antigen.

We have further found that covalently linked IMP/MC complexes comprising nanocarrier particles are highly active immunomodulators. Prior teaching in the art indicates that immunostimulatory oligonucleotides tightly bound to microparticles and nanoparticles are not effective (Manzel et al., supra). In view of this understanding in the art, we believe that our results would be surprising and unexpected to one of skill in the art.

The immunomodulatory polynucleotide/microcarrier (IMP/MC) complexes of the invention may be covalently or non-covalently linked, and comprise a microcarrier (e.g., a carrier of less than about 10 μm size) that is insoluble and/or filterable in water. Microcarriers are generally solid phase (e.g., polylactic acid beads), although biodegradable liquid phase microcarriers (e.g., an oil in water emulsion comprising a biodegradable polymer or oil) are also useful. The IMP may be modified to allow or augment binding to the MC (e.g., by incorporation of a free sulfhydryl for covalent crosslinking or addition of a hydrophobic moiety such as cholesterol for hydrophobic bonding).

The invention provides new compositions comprising an IMP covalently linked to a biodegradable microcarrier to form a covalent IMP/MC complex. Linkage between the IMP and MC may be direct (e.g., via disulfide bond between sulfhydryls on the IMP and MC) or the constituents may be linked by a crosslinking moiety of one or more atoms separating the bonds to the IMP and MC.

Also provided are compositions comprising an IMP non-covalently linked to a microcarrier to provide a non-covalent IMP/MC complex. Non-covalent IMP/MC complexes generally comprise an IMP that has been modified to allow binding to the microcarrier (e.g., by addition of a cholesterol moiety to the IMP to allow hydrophobic binding to oil or lipid based microcarrier) although, as would be understood by those in the art, the properties of the native IMP may be used to bind to the microcarrier (e.g., electrostatic binding to a cationic microcarrier such as cationic poly(lactic acid, glycolic acid) copolymer).

The invention also provides methods for modulating an immune response in an individual by administering an IMP/MC complex to the individual.

Further provided are kits for practicing the methods of the invention. The kits comprise any of the IMP/MC complexes and/or components for the IMP/MC complex in suitable packaging and may also contain instructions for administering an IMP/MC complex for immunomodulation in a subject.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

DEFINITIONS

As used herein, the singular form "a", "an", and "the" includes plural references unless indicated otherwise. For example, "an" ISS includes one or more ISS.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphoester linkages, although alternate linkages, such as phosphorothioate esters may also be used in oligonucleotides. A nucleoside consists of a purine (adenine, guanine or inosine, or derivative thereof) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The instant disclosure uses single letters to indicate bases of a nucleotide sequence, where A is adenine, G is guanine, C is cytosine, T is thymine, U is uracil, I is inosine, R is a purine, and Y is a pyrimidine.

The term "ISS" as used herein refers to polynucleotide sequences, alone and/or complexed with MC, that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Preferably, the ISS sequences preferentially activate a Th1-type response. A polynucleotide for use in the invention contains at least one ISS. As used herein, "ISS" is also a shorthand term for an ISS-containing polynucleotide.

The term "immunomodulatory polynucleotide" or "IMP", as used herein, refers to a polynucleotide comprising at least one ISS. In certain embodiments, the IMP is an ISS.

The term "microcarrier" refers to a biodegradable particulate composition which is insoluble in water and which has a size of less than about 150, 120 or 100 μm in size, more commonly less than about 50-60 μm, preferably less than about 10, 5, 2.5, 2 or 1.5 μm. Microcarriers include "nanocarriers", which are microcarriers have a size of less than about 1 preferably less than about 500 nm. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers which deviate from spherical shape are also acceptable (e.g., elipsoid, rod-shaped, etc.). Due to their insoluble nature (with respect to water), microcarriers are filterable from water and water-based (aqueous) solutions.

The "size" of a microcarrier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ± about 5-10% of the stated measurement. Size characteristics may also be determined by dynamic light scattering or obscuration techniques. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 μm to about 10 nm in size pass through a 10 μm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

A microcarrier is considered "biodegradable" if it is degradable or erodable under normal mammalian physiological conditions. Generally, a microcarrier is considered biodegradable if it is degraded (i.e., loses at least 5% of its mass and/or average polymer length) after a 72 hour incubation at 37° C. in normal human serum. Accordingly, and conversely, a microcarrier is considered "nonbiodegradable" if it is not degraded or eroded under normal mammalian physiological conditions. Generally, a microcarrier is considered nonbiodegradable if it not degraded (i.e., loses less than 5% of its mass and/or average polymer length) after at 72 hour incubation at 37° C. in normal human serum.

The term "immunomodulatory polynucleotide/microcarrier complex" or "IMP/MC complex" refers to a complex of an ISS-containing polynucleotide comprising a 5'-CG-3' sequence and a microcarrier of the invention. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the IMP.

As used herein, "immunomodulatory" can refer to the polynucleotide and/or the complex. Thus, IMP/MC complex may exhibit immunomodulatory activity even when the polynucleotide of the IMP/MC complex has a sequence that, if presented as a polynucleotide alone, does not exhibit comparable immunomodulatory activity. In some embodiments, when presented alone, a polynucleotide of an IMP/MC complex does not have "isolated immunomodulatory activity," or has "inferior isolated immunomodulatory activity," (i.e., when compared to the IMP/MC complex). The "isolated immunomodulatory activity" of a polynucleotide is determined by measuring the immunomodulatory activity of the isolated polynucleotide having the same nucleic acid backbone (e.g., phosphorothioate, phosphodiester, chimeric) using standard assays which indicate at least one aspect of an immune response, such as those described herein.

The term "immunomodulatory" or "modulating an immune response" as used herein includes immunostimulatory as well as immunosuppressive effects. Immunomodulation is primarily a qualitative alteration in an overall immune response, although quantitative changes may also occur in conjunction with immunomodulation. An immune response that is immunomodulated according to the present invention is one that is shifted towards a "Th1-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen, and can be detected at the biochemical level by increased levels of Th1-associated cytokines such as IFN-γ, IL-2, IL-12, and TNF-β, as well as IFN-α and IL-6, although IL-6 may also be associated with Th2-type responses as well. Th1-type immune responses are generally associated with the production of cytotoxic lymphocytes (CTLs) and low levels or transient production of antibody. Th2-type immune responses are generally associated with higher levels of antibody production, including IgE production, an absence of or minimal CTL production, as well as expression of Th2-associated cytokines such as IL-4. Accordingly, immunomodulation in accordance with the invention may be recognized by, for example, an increase in IFN-γ and/or a decrease in IgE production in an individual treated in accordance with the methods of the invention as compared to the absence of treatment.

The term "conjugate" refers to a complex in which an ISS-containing polynucleotide and an antigen are linked. Such conjugate linkages include covalent and/or non-covalent linkages.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with ISS include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g. sterols, fatty acids, and phospholipids), polysaccharides such as those used in Hemophilus influenza vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g. antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant peptides, crude peptide extracts, or peptides in a partially purified or unpurified active state (such as peptides that are a part of attenuated or inactivated viruses, cells, or micro-organisms, or fragments of such peptides). An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of an IMP/MC complex to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited, to histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) *Otolaryngol. Clin. North Am.* 31:111-127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

An "individual" is a vertebrate, preferably a mammal, more preferably a human. Mammals include, but are not limited to, humans, primates, farm animals, sport animals, rodents and pets. Vertebrates also include, but are not limited to, birds (i.e., avian individuals) and reptiles (i.e., reptilian individuals).

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to an antigen, an effective amount of an IMP/MC complex is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, *Hymenoptera* sting allergies, and drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival, if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an IMP/MC complex refers to the amount of a given antibody measured at a time point after administration of IMP/MC complex.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, an IMP/MC complex administered with an antigen or including an antigen which suppresses histamine release reduced histamine release as compared to, for example, histamine release induced by antigen alone.

As used herein, the term "comprising" and its cognates are used in their inclusive sense; that is, equivalent to the term "including" and its corresponding cognates.

Compositions of the Invention

The invention provides new compositions for modulating immune response in individuals. The new compositions are immunomodulatory polynucleotide/microcarrier (IMP/MC) complexes which comprise an ISS-containing polynucleotide complexed to a biodegradable microcarrier. IMP/MC complexes may be covalent complexes, in which the IMP portion of the complex is covalently bonded to the MC, either directly or via a linker (i.e., indirectly), or they may be non-covalent complexes.

Immunomodulatory Polynucleotides

In accordance with the present invention, the immunomodulatory polynucleotide comprises the sequence 5'-cytosine, guanine-3', can contain at least one ISS, and can contain multiple ISSs. The ISSs can be adjacent within the polynucleotide, or they can be separated by additional nucleotide bases within the polynucleotide. Accordingly, an IMP may contain combinations of any one or more ISS described herein, including those with modifications. In certain embodiments, the IMP consists of an ISS. The IMP affects a measurable immune response, as measured in vitro, in vivo and/or ex vivo, when complexed with a microcarrier. In some embodiments, the IMP is not active or, in some embodiments, is less active, as measured in vitro, in vivo and/or ex vivo, when uncomplexed.

The ISS can be of any length greater than 6 bases or base pairs and generally comprises the sequence 5'-cytosine, guanine-3', preferably greater than 15 bases or base pairs, more preferably greater than 20 bases or base pairs in length. As is well-known in the art, the cytosine of the 5'-cytosine, guanine-3' sequence is generally unmethylated, especially at the C-5 position. As the term "ISS" conveys and is defined, an ISS effects an immune response and as such, in certain embodiments, methylation of the cytosine may be permitted, for example, at the N-4 position. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As indicated in polynucleotide sequences below, an ISS may comprise (i.e., contain one or more of) the sequence 5'-T, C, G-3'. Accordingly, an ISS may comprise 5'-CG-3' and/or 5'-TCG-3'. In some embodiments, an ISS may comprise the sequence 5'-C, G, pyrimidine, pyrimidine, C, G-3' (such as 5'-CGTTCG-3'). In some embodiments, an ISS may comprise the sequence 5'-C, G, pyrimidine, pyrimidine, C, G, purine, purine-3'. In some embodiments, an ISS comprises the sequence 5'-purine, purine, C, G, pyrimidine, pyrimidine-3' (such as 5'-AACGTT-3').

In some embodiments, an ISS may comprise the sequence 5'-purine, T, C, G, pyrimidine, pyrimidine-3'.

In some embodiments, the ISS comprises any of the following sequences:

GACGCTCC; GACGTCCC; GACGTTCC; GACGCCCC; AGCGTTCC;
AGCGCTCC; AGCGTCCC; AGCGCCCC; AACGTCCC; AACGCCCC;
AACGTTCC; AACGCTCC; GGCGTTCC; GGCGCTCC; GGCGTCCC;
GGCGCCCC; GACGCTCG; GACGTCCG; GACGCCCG; GACGTTCG;
AGCGCTCG; AGCGTTCG; AGCGTCCG; AGCGCCCG; AACGTCCG;
AACGCCCG; AACGTTCG; AACGCTCG; GGCGTTCG; GGCGCTCG;
GGCGTCCG; GGCGCCCG.

In some embodiments, the ISS comprises any of the following sequences:

GACGCT; GACGTC; GACGTT; GACGCC; GACGCU; GACGUC;
GACGUU; GACGUT; GACGTU; AGCGTT; AGCGCT; AGCGTC;
AGCGCC; AGCGUU; AGCGCU; AGCGUC; AGCGUT; AGCGTU;
AACGTC; AACGCC; AACGTT; AACGCT; AACGUC; AACGUU;
AACGCU; AACGUT; AACGTU; GGCGTT; GGCGCT; GGCGTC;
GGCGCC; GGCGUU; GGCGCU; GGCGUC; GGCGUT; GGCGTU.

In some embodiments, the ISS comprises any of the following sequences:

GABGCT; GABGTC; GABGTT; GABGCC; GABGCU; GABGUC;
GABGUU; GABGUT; GABGTU; AGBGTT; AGBGCT; AGBGTC;
AGBGCC; AGBGUU; AGBGCU; AGBGUC; AGBGUT; AGBGTU;
AABGTC; AABGCC; AABGTT; AABGCT; AABGUC; AABGUU;
AABGCU; AABGUT; AABGTU; GGBGTT; GGBGCT; GGBGTC;
GGBGCC; GGBGUU; GGBGCU; GGBGUC; GGBGUT; GGBGTU, where B is 5-bromocytosine.

In some embodiments, the ISS comprises any of the following sequences:

GABGCTCC; GABGTCCC; GABGTTCC; GABGCCCC; AGBGTTCC;
AGBGCTCC; AGBGTCCC; AGBGCCCC; AABGTCCC; AABGCCCC;
AABGTTCC; AABGCTCC; GGBGTTCC; GGBGCTCC; GGBGTCCC;
GGBGCCCC; GABGCTCG; GABGTCCG; GABGCCCG; GABGTTCG;
AGBGCTCG; AGBGTTCG; AGBGTCCG; AGBGCCCG; AABGTCCG;
AABGCCCG; AABGTTCG; AABGCTCG; GGBGTTCG; GGBGCTCG;
GGBGTCCG; GGBGCCCG; GABGCTBG; GABGTCBG; GABGCCBG;
GABGTTBG; AGBGCTBG; AGBGTTBG; AGBGTCBG; AGBGCCBG;
AABGTCBG; AABGCCBG; AABGTTBG; AABGCTBG; GGBGTTBG;
GGBGCTBG; GGBGTCBG; GGBGCCBG, where B is 5-bromocytosine.

In some embodiments, the ISS comprises any of the following sequences:

GABGCUCC; GABGUCCC; GABGUTCC; GABGTUCC; GABGUUCC;
AGBGUUCC; AGBGTUCC; AGBGUTCC; AGBGCUCC; AGBGUCCC;
AABGUCCC; AABGUUCC; AABGUTCC; AABGTUCC; AABGCUCC;
GGBGUUCC; GGBGUTCC; GGBGTUCC; GGBGCUCC; GGBGUCCC;
GABGCUCG; GABGUCCG; GABGUUCG; GABGUTCG; GABGTUCG;
AGBGCUCG; AGBGUUCG; AGBGUTCG; AGBGTUCG; AGBGUCCG;
AABGUCCG; AABGUUCG; AABGUTCG; AABGTUCG; AABGCUCG;
GGBGUUCG; GGBGUTCG; GGBGTUCG; GGBGCUCG; GGBGUCCG;
GABGCUBG; GABGUCBG; GABGUUBG; GABGUTBG; GABGTUBG;
AGBGCUBG; AGBGUUBG; AGBGUCBG; AGBGUTBG; AGBGTUBG;
AABGUCBG; AABGUUBG; AABGUTBG; AABGTUBG; AABGCUBG;
GGBGUUBG; GGBGUTBG; GGBGTUBG; GGBGCUBG; GGBGUCBG, where B is 5-bromocytosine.

In some embodiments, the immunomodulatory polynucleotide comprises the sequence 5'-TGACTGTGAACGTTCGAGATGA-3' (SEQ ID NO:1). In other embodiments, the ISS comprises any of the sequences:

| | |
|---|---|
| 5'-TGACCGTGAACGTTCGAGATGA-3'; | (SEQ ID NO: 2) |
| 5'-TCATCTCGAACGTTCCACAGTCA-3'; | (SEQ ID NO: 3) |
| 5'-TGACTGTGAACGTTCCAGATGA-3' | (SEQ ID NO: 4) |
| 5'-TCCATAACGTTCGCCTAACGTTCGTC-3' | (SEQ ID NO: 5) |
| 5'-TGACTGTGAABGTTCCAGATGA-3', | (SEQ ID NO: 6) | where B is 5-bromocytosine;

| | |
|---|---|
| 5'-TGACTGTGAABGTTCGAGATGA-3', | (SEQ ID NO: 7) | where B is 5-bromocytosine;

| | |
|---|---|
| 5'-TGACTGTGAABGTTBGAGATGA-3', | (SEQ ID NO: 8) | where B is 5-bromocytosine and

```
5'-TCGAGCGTTCT-3';            (SEQ ID NO: 21)

5'-ATCGACTCTCGAGCGTTCTC-3'    (SEQ ID NO: 22)
and

5'-TCGTCGTTTTGTCGTTTTGTCGTT-3'.  (SEQ ID NO: 23)
```

In some embodiments, an IMP (or ISS) can be 7 bases (or base pairs) or more. Accordingly, in some embodiments, the ISS comprises the sequence 5'-TCGX$_1$X$_2$X$_3$X$_4$-3' or 5'-UCGX$_1$X$_2$X$_3$X$_4$-3' wherein X$_1$, X$_2$, X$_3$, X$_4$ are nucleotides. In some embodiments, the ISS comprises any of the following sequences: 5'-TCGTTTT-3'; 5'-TCGAAAA-3; 5'-TCGCCCC-3'; 5'-TCGGGGG-3'; 5'-TCGUUUU-3'; 5'-TCGIIII-3; 5'-UCGTTTT-3'; 5'-UCGAAAA-3'; 5'-UCGCCCC-3'; 5'-UCGGGGG-3'; 5'-UCGUUUU-3'; 5'-UCGIIII-3'. In some embodiments, the ISS comprises the sequence 5'-X$_1$TCGX$_2$X$_3$X$_4$-3' or 5'-X$_1$UCGX$_2$X$_3$X$_4$-3', wherein X$_1$, X$_2$, X$_3$, X$_4$ are nucleotides. In some embodiments, the ISS comprises any of the following sequences: 5'-TTCGTTT-3'; 5'-ATCGATT-3'; 5'-TUCGTTT-3'; 5'-AUCGATT-3'. In some embodiments, the ISS comprises the sequence 5'-X$_1$X$_2$TCGX$_3$X$_4$-3' or 5'-X$_1$X$_2$UCGX$_3$X$_4$-3', wherein X$_1$, X$_2$, X$_3$, X$_4$ are nucleotides. In some embodiments, the ISS comprises any of the following sequences: 5'-TTTCGTT-3'; 5'-AATCGAT-3'; 5'-TTUCGTT-3'; 5'-AAUCGAT-3'.

In some embodiments, the ISS comprises the sequence 5'-TCGTCGX$_1$-3', wherein X$_1$ is a nucleotide. In some embodiments, the ISS comprises any of the following sequences: 5'-TCGTCGA-3'; 5'-TCGTCGC-3'; 5'-TCGTCGG-3; 5'-TCGTCGT-3; 5'-TCGTCGU-3; 5'-TCGTCGI-3'. In some embodiments, the ISS comprises the sequence 5'-TCGUCGX$_1$-3', 5'-UCGTCGX$_1$-3', or 5'-UCGUCGX$_1$-3', wherein X$_1$ is a nucleotide. In some embodiments, the ISS comprises any of the following sequences: 5'-TCGUCGA-3'; 5'-TCGUCGC-3'; 5'-TCGUCGG-3'; 5'-TCGUCGT-3'; 5'-TCGUCGU-3'; 5'-TCGUCGI-3'; 5'-UCGTCGA-3'; 5'-UCGTCGC-3'; 5'-UCGTCGG-3'; 5'-UCGTCGT-3'; 5'-UCGTCGU-3'; 5'-UCGTCGI-3'; 5'-UCGUCGA-3'; 5'-UCGUCGC-3'; 5'-UCGUCGG-3'; 5'-UCGUCGT-3'; 5'-UCGUCGU-3'; 5'-UCGUCGI-3'.

In some embodiments, the ISS comprises the sequence 5'-T mC GX$_1$X$_2$X$_3$X$_4$-3' or 5'-U mC GX$_1$X$_2$X$_3$X$_4$-3', wherein X$_1$, X$_2$, X$_3$, X$_4$ are nucleotides and wherein mC is a modified cytosine as described herein. In some embodiments, the ISS comprises the sequence 5'-X$_1$T mC GX$_2$X$_3$X$_4$-3' or 5'-X$_1$U mC GX$_2$X$_3$X$_4$-3', wherein X$_1$, X$_2$, X$_3$, X$_4$ are nucleotides. In some embodiments, the ISS comprises the sequence 5'-X$_1$X$_2$T mC GX$_3$X$_4$-3' or 5'-X$_1$X$_2$U mC GX$_3$X$_4$-3', wherein X$_1$, X$_2$, X$_3$, X$_4$ are nucleotides.

In some embodiments, the ISS comprises the sequence 5'-T mC GTCGX$_1$-3', 5'-T mC GUCGX$_1$-3', 5'-U mC GTCGX$_1$-3' or 5'-U mC GUCGX$_1$-3', wherein X$_1$ is a nucleotide. In some embodiments, the ISS comprises the sequence 5'-TCGT mC GX$_1$-3', 5'-UCGT mC GX$_1$-3'. 5'-TCGU mC GX$_1$-3' or 5'-UCGU mC GX$_1$-3', wherein X$_1$ is a nucleotide. In some embodiments, the ISS comprises the sequence 5'-T mC GT mC GX$_1$-3', 5'-U mC GT mC GX$_1$-3', 5'-T mC GU mC GX$_1$-3' or 5'-U mC GU mC GX$_1$-3', wherein X$_1$ is a nucleotide. As described herein, a modified cytosine (mC) includes addition of an electron-withdrawing moiety to C-5 and/or C-6 of a cytosine, including, but not limited to, C-5 halogenated cytosine, such as 5-bromocytosine.

Thus, in some embodiments, the ISS comprises any of the following sequences: 5'-TBGTTTT-3'; 5'-TBGAAAA-3'; 5'-TBGCCCC-3'; 5'-TBGGGGG-3'; 5'-TBGUUUU-3'; 5'-TBGIIII-3'; 5'-TBGTCGA-3'; 5'-TBGTCGC-3'; 5'-TBGTCGG-3'; 5'-TBGTCGT-3'; 5'-TBGTCGU-3'; 5'-TBGTCGI-3'; 5'-TCGTBGA-3'; 5'-TCGTBGC-3'; 5'-TCGTBGG-3'; 5'-TCGTBGT-3'; 5'-TCGTBGU-3'; 5'-TCGTBGI-3'; 5'-TBGTBGA-3'; 5'-TBGTBGC-3'; 5'-TBGTBGG-3'; 5'-TBGTBGT-3', 5'-TBGTBGU-3'; 5'-TBGTBGI-3'; where B is 5-bromocytosine.

In some embodiments, the polynucleotide of the IMP/MC consists of the sequence 5'-TCGX$_1$X$_2$X$_3$X$_4$-3' or 5'-UCGX$_1$X$_2$X$_3$X$_4$-3' wherein X$_1$, X$_2$, X$_3$, X$_4$ are nucleotides. In some embodiments, the polynucleotide of the IMP/MC consists of any of the following sequences: 5'-TCGTTTT-3'; 5'-TCGAAAA-3'; 5'-TCGCCCC-3'; 5'-TCGGGGG-3'; 5'-TCGUUUU-3'; 5'-TCGIIII-3'; 5'-UCGTTTT-3'; 5'-UCGAAAA-3'; 5'-UCGCCCC-3; 5'-UCGGGGG-3'; 5'-UCGUUUU-3'; 5'-UCGIIII-3'.

In some embodiments, the polynucleotide of the IMP/MC consists of the sequence 5'-X$_1$TCGX$_2$X$_3$X$_4$-3' or 5'-X$_1$UCGX$_2$X$_3$X$_4$-3', wherein X$_1$, X$_2$, X$_3$, X$_4$ are nucleotides. In some embodiments, the polynucleotide of the IMP/MC consists of any of the following sequences: 5'-TTCGTTT-3'; 5'-ATCGATT-3'; 5'-TUCGTTT-3'; 5'-AUCGATT-3'.

In some embodiments, the polynucleotide of the IMP/MC consists of the sequence 5'-X$_1$X$_2$TCGX$_3$X$_4$-3' or 5'-X$_1$X$_2$UCGX$_3$X$_4$-3', wherein X$_1$, X$_2$, X$_3$, X$_4$ are nucleotides. In some embodiments, the polynucleotide of the IMP/MC consists of any of the following sequences: 5'-TTTCGTT-3'; 5'-AATCGAT-3'; 5'-TTUCGTT-3'; 5'-AAUCGAT-3'.

In some embodiments, the polynucleotide of the IMP/MC consists of the sequence 5'-TCGTCGX$_1$-3', wherein X$_1$ is a nucleotide. In some embodiments, the polynucleotide of the IMP/MC consists of the sequence 5'-TCGTCGA-3'; 5'-TCGTCGC-3'; 5'-TCGTCGG-3'; 5'-TCGTCGT-3'; 5'-TCGTCGU-3'; 5'-TCGTCGI-3'. In some embodiments, the polynucleotide of the IMP/MC consists of the sequence 5'-TCGUCGX$_1$-3', 5'-UCGTCGX$_1$-3', or 5'-UCGUCGX$_1$-3', wherein X$_1$ is a nucleotide. In some embodiments, the polynucleotide of the IMP/MC consists of any of the following sequences: 5'-TCGUCGA-3'; 5'-TCGUCGC-3'; 5'-TCGUCGG-3'; 5'-TCGUCGT-3'; 5'-TCGUCGU-3'; 5'-TCGUCGI-3'; 5'-UCGTCGA-3'; 5'-UCGTCGC-3'; 5'-UCGTCGG-3'; 5'-UCGTCGT-3'; 5'-UCGTCGU-3'; 5'-UCGTCGI-3'; 5'-UCGUCGA-3'; 5'-UCGUCGC-3'; 5'-UCGUCGG-3'; 5'-UCGUCGT-3'; 5'-UCGUCGU-3'; 5'-UCGUCGI-3'.

In some embodiments, the polynucleotide of the IMP/MC consists of the sequence 5'-T mC GX$_1$X$_2$X$_3$X$_4$-3' or 5'-U mC GX$_1$X$_2$X$_3$X$_4$-3', wherein X$_1$, X$_2$, X$_3$, X$_4$ are nucleotides and wherein mC is a modified cytosine as described herein. In some embodiments, the polynucleotide of the IMP/MC consists of the sequence 5'-X$_1$T mC GX$_2$X$_3$X$_4$-3' or 5'-X$_1$U mC GX$_2$X$_3$X$_4$-3', wherein X$_1$, X$_2$, X$_3$, X$_4$ are nucleotides. In some embodiments, the polynucleotide of the IMP/MC consists of the sequence 5'-X$_1$X$_2$T mC GX$_3$X$_4$-3' or 5'-X$_1$X$_2$U mC GX$_3$X$_4$-3', wherein X$_1$, X$_2$, X$_3$, X$_4$ are nucleotides.

In some embodiments, the polynucleotide of the IMP/MC consists of the sequence 5'-T mC GTCGX$_1$-3', 5'-T mC GUCGX$_1$-3', 5'-U mC GTCGX$_1$-3' or 5'-U mC GUCGX$_1$-3', wherein X$_1$ is a nucleotide. In some embodiments, the polynucleotide of the IMP/MC consists of the sequence 5'-TCGT mC GX$_1$-3', 5'-UCGT mC GX$_1$-3'. 5'-TCGU mC GX$_1$-3' or 5'-UCGU mC GX$_1$-3', wherein X$_1$ is a nucleotide. In some embodiments, the polynucleotide of the IMP/MC consists of the sequence 5'-T mC GT mC GX$_1$-3', 5'-U mC GT mC GX$_1$-3', 5'-T mC GU mC GX$_1$-3' or 5'-U mC GU mC GX$_1$-3', wherein X$_1$ is a nucleotide. As described herein, a modified cytosine (mC) includes addition of an electron-withdrawing moiety to C-5 and/or C-6 of a cytosine, including, but not limited to, C-5 halogenated cytosine, such as 5-bromocytosine.

Thus, in some embodiments, the polynucleotide of the IMP/MC consists of any of the following sequences: 5'-TB-GTTTT-3'; 5'-TBGAAAA-3'; 5'-TBGCCCC-3'; 5'-TBGGGGG-3'; 5'-TBGUUUU-3'; 5'-TBGIIII-3'; 5'-TB-GTCGA-3'; 5'-TBGTCGC-3'; 5'-TBGTCGG-3'; 5'-TB-GTCGT-3'; 5'-TBGTCGU-3'; 5'-TBGTCGI-3'; 5'-TCGT-BGA-3'; 5'-TCGTBGC-3'; 5'-TCGTBGG-3'; 5'-TCGTBGT-3'; 5'-TCGTBGU-3; 5'-TCGTBGI-3'; 5'-TBGTBGA-3'; 5'-TBGTBGC-3'; 5'-TBGTBGG-3'; 5'-TBGTBGT-3', 5'-TB-GTBGU-3'; 5'-TBGTBGI-3'; where B is 5-bromocytosine.

An ISS and/or IMP may contain modifications. Modifications of ISS include any known in the art, but are not limited to, modifications of the 3'OH or 5'OH group, modifications of the nucleotide base, modifications of the sugar component, and modifications of the phosphate group. Various such modifications are described below.

It is preferred that cytosines present in the ISS are not methylated, however, in certain embodiments the ISS may contain on or more methylated cytosines. In such embodiments it is preferred that the cytosine of the 5'-CG-3' of the ISS is not methylated at the C-5 position. However, methylation at position N-4 is contemplated in those ISS with methylated cytosines.

An ISS and/or IMP may be single stranded or double stranded DNA, as well as single or double-stranded RNA or other modified polynucleotides. An ISS may or may not include one or more palindromic regions, which may be present in the motifs described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, oligonucleotides of the present invention comprise phosphodiester and/or phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine). See, for example, International Patent Application No. WO 99/62923.

The ISS and/or IMP can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS and/or IMP can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular IMP can be isolated, synthesized through recombinant methods, or chemically synthesized. Where the circular IMP is obtained through isolation or through recombinant methods, the IMP will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) *DNA* 3:401 and U.S. Pat. No. 4,458,066.

The ISS and/or IMP can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141). Oligonucleotides with phosphorothioate backbones can be more immunogenic than those with phosphodiester backbones and appear to be more resistant to degradation after injection into the host. Braun et al. (1988) *J. Immunol.* 141:2084-2089; and Latimer et al. (1995) *Mol. Immunol.* 32:1057-1064.

ISS-containing polynucleotides and/or IMPs used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS and/or IMP.

The heterocyclic bases, or nucleic acid bases, which are incorporated in the ISS and/or IMP can be the naturally-occurring principal purine and pyrimidine bases, (namely uracil, thymine, cytosine, inosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2,3-d]pyrimidin-5-yl, 2-amino-4-oxopyrolo[2.3-d]pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS and/or IMP may comprise at least one modified base as described, for example, in the commonly owned international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Modified cytosines can include, but are not limited to, azacytosine, 5-bromocytosine, 5-chlorocytosine, chlorinated cytosine, cyclocytosine, cytosine arabinoside, 5-fluorocytosine, fluoropyrimidine, 5,6-dihydrocytosine, 5-iodocytosine, hydroxyurea, 5-nitrocytosine, 5-hydroxycytosine and any other pyrimidine analog or modified pyrimidine. Preferred modified uracils are modified at C-5 and/or C-6, preferably with a halogen, and include, but are not limited to, bromouracil such as 5-bromouracil, chlorouracil such as 5-chlorouracil, fluorouracil such as 5-fluorouracil, iodouracil such as 5-iodouracil, and hydroxyuracil. Also see, Kandimalla et al., 2001, *Bioorg. Med. Chem.* 9:807-813. See, for example, International Patent Application No. WO 99/62923. Other examples of base modifications include the addition of one or more thiol groups to the base including, but not limited to, 6-thio-guanine, 4-thio-thymine and 4-thio-uracil. Additionally, some IMPs may comprise modified bases such as 7-deazaguanosine in place of any guanosine residue, or a modified cytosine selected from N-4-ethylcytosine or N-4-methylcytosine in place of any cytosine residue, including the cytosine of the 5'-CG-3'.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

As described herein, an IMP is any length greater than 6 bases or base pairs. Accordingly, in some embodiments, an IMP is less than about any of the following lengths (in bases or base pairs): 10,000; 5,000; 2500; 2000; 1500; 1250; 1000; 750; 500; 300; 250; 200; 175; 150; 125; 100; 75; 50; 25; 10; 8. In some embodiments, an IMP is greater than about any of the following lengths (in bases or base pairs): 6, 7; 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the ISS can be any of a range of sizes having an upper limit of 10,000; 5,000; 2500; 2000; 1500; 1250; 1000; 750; 500; 300; 250; 200; 175; 150; 125; 100; 75; 50; 25; 10; 8 or 7 and an independently selected lower limit of 7; 8; 10; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) *Nature* 374:546-549; Yamamoto et al. (1992a); Ballas et al. (1996); Klinman et al. (1997); Sato et al. (1996); Pisetsky (1996a); Shimada et al. (1986) *Jpn. J. Cancer Res.* 77:808-816; Cowdery et al. (1996) *J. Immunol.* 156: 4570-4575; Roman et al. (1997); and Lipford et al. (1997a). These methods are likewise applicable to assessing immunomodulatory activity of an IMP/MC complex.

One property of an IMP is the "isolated immunomodulatory activity" associated with the nucleotide sequence of the IMP. As noted above, the present inventors have discovered that, surprisingly, IMP/MC complexes exhibit immunomodulatory activity even when the IMP has a sequence that, if presented as a polynucleotide alone, does not exhibit comparable immunomodulatory activity.

In some embodiments, an IMP of an IMP/MC complex does not have "isolated immunomodulatory activity," or has "inferior isolated immunomodulatory activity," (i.e., when compared to the IMP/MC complex), as described below.

The "isolated immunomodulatory activity" of an IMP is determined by measuring the immunomodulatory activity of an isolated polynucleotide having the primary sequence of the IMP, and having the same nucleic acid backbone (e.g., phosphorothioate, phosphodiester, chimeric). To determine the independent immunomodulatory activity of, for example, an IMP in the IMP/MC complex, a test polynucleotide having the same sequence (e.g., 5'-TCGTCGA-3') and same backbone structure (e.g., phosphorothioate) is synthesized using routine methods, and its immunomodulatory activity (if any) is measured. Immunomodulatory activity can be determined using standard assays which indicate various aspects of the immune response, such as those described herein. For example, the human PBMC assay described herein is used. To account for donor variation, typically the assay is carried out in multiple donors. A polynucleotide does not have immunomodulatory activity (and the corresponding IMP does not have "isolated immunomodulatory activity") when the amount of IFN-γ secreted by PBMCs contacted with the polynucleotide is not significantly greater (e.g., less than about 2-fold greater) in the majority of donors than in the absence of the test compound or, (in some embodiments) in the presence of an inactive control compound (e.g., 5'-TGACTGTGAACCTTAGAGATGA-3' (SEQ ID NO:10)).

To compare the immunomodulatory activity of an IMP/MC complex and an isolated polynucleotide, immunomodulatory activity is measured, preferably, but not necessarily, using the human PBMC assay. Usually, the activity of two compounds is compared by assaying them in parallel under the same conditions (e.g., using the same cells), usually at a concentration of about 20 μg/ml. Generally, concentration is determined by measuring absorbance at 260 nm and using the conversion 0.5 $OD_{260}$/ml=20 μg/ml. This normalizes the amount of total nucleic acid in the test sample. Alternatively, concentration or weight can be measured by other methods known in the art.

An IMP of an IMP/MC complex is characterized as having "inferior immunomodulatory activity," when the test polynucleotide has less activity than the IMP/MC complex to which it is compared. Preferably the isolated immunomodulatory activity of the test polynucleotide is no more than about 50% of the activity of the IMP/MC complex, more preferably no more than about 20%, most preferably no more than about 10% of the activity of the IMP/MC complex, or in some embodiments, even less.

Microcarriers

Microcarriers useful in the invention are less than about 150, 120 or 100 μm in size, more commonly less than about 50-60 μm in size, preferably less than about 10 μm in size, and are insoluble in pure water. Microcarriers used in the invention are biodegradable. Microcarriers are commonly solid phase, such as "beads" or other particles, although biodegradable liquid phase microcarriers such as oil in water emulsions comprising a biodegradable polymers or oils are also contemplated. A wide variety of biodegradable materials acceptable for use as microcarriers are known in the art.

Microcarriers for use in the compositions or methods of the invention are generally less than about 10 μm in size (e.g., have an average diameter of less than about 10 μm, or at least about 97% of the particles pass through a 10 μm screen filter), and include nanocarriers (i.e., carriers of less than about 1 μm size). Preferably, microcarriers are selected having sizes within an upper limit of about 9, 7, 5, 2, or 1 μm or 900, 800, 700, 600, 500, 400, 300, 250, 200, or 100 nm and an independently selected lower limit of about 4, 2, or 1 μm or about 800, 600, 500, 400, 300, 250, 200, 150, 100, 50, 25, or 10 nm, where the lower limit is less than the upper limit. In some embodiments, the microcarriers have a size of about 1.0-1.5 μm, about 1.0-2.0 μm or about 0.9-1.6 μm. In certain preferred embodiments, the microcarriers have a size of about 10 nm to about 5 μm or about 25 nm to about 4.5 μm, about 1 μm, about 1.2 μm, about 1.4 μm, about 1.5 μm, about 1.6 μm, about 1.8 μm, about 2.0 μm, about 2.5 μm or about 4.5 μm. When the microcarriers are nanocarriers, preferred embodiments include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly (glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro [5.5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) *Biotechnol. Bioeng.* 1996:102); and polyamides such as poly(lactic acid-co-lysine).

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vaccum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

Antigen

IMP/MC complexes may be prepared which comprise antigen or which are antigen-free, i.e., IMP/MC complexes not linked to an antigen. Any antigen may be used in the preparation of IMP/MC complexes comprising antigen.

In some embodiments, the antigen is an allergen. Examples of recombinant allergens are provided in Table 1. Preparation of many allergens is well-known in the art, including, but not limited to, preparation of ragweed pollen allergen Antigen E (Amb aI) (Rafnar et al. (1991) *J. Biol. Chem.* 266:1229-1236), major dust mite allergens Der pI and Der PII (Chua et al. (1988) *J. Exp. Med.* 167:175-182; Chua et al. (1990) *Int. Arch. Allergy Appl. Immunol.* 91:124-129), white birch pollen Bet vl (Breiteneder et al. (1989) *EMBO J.* 8:1935-1938), domestic cat allergen Fel d I (Rogers et al. (1993) *Mol. Immunol.* 30:559-568), and protein antigens from tree pollen (El-sayed et al. (1991) *Scand. J. Clin. Lab. Invest. Suppl.* 204:17-31). As indicated, allergens from trees are known, including allergens from birch, juniper and Japanese cedar. Preparation of protein antigens from grass pollen for in vivo administration has been reported. Malley (1989) *J. Reprod. Immunol.* 16:173-186. As Table 1 indicates, in some embodiments, the allergen is a food allergen such as peanut allergen, for example Ara h I, and in some embodiments, the allergen is a grass allergen such as a rye allergen, for example Lol p 1. Table 1 shows a list of allergens that may be used.

TABLE 1

RECOMBINANT ALLERGENS

| Group | Allergen | Reference |
|---|---|---|
| ANIMALS: CRUSTACEA | | |
| Shrimp/lobster | tropomyosin Pan s I | Leung et al. (1996) J. Allergy Clin. Immunol. 98: 954-961 Leung et al. (1998) Mol. Mar. Biol. Biotechnol. 7: 12-20 |
| INSECTS | | |
| Ant | Sol i 2 (venom) | Schmidt et al. J Allergy Clin Immunol., 1996, 98: 82-8 |
| Bee | Phospholipase A2 (PLA) | Muller et al. J Allergy Clin Immunol, 1995, 96: 395-402 Forster et al. J Allergy Clin Immunol, 1995, 95: 1229-35 Muller et al. Clin Exp Allergy, 1997, 27: 915-20 |
| | Hyaluronidase (Hya) | Soldatova et al. J Allergy Clin Immunol, 1998, 101: 691-8 |
| Cockroach | Bla g Bd9OK | Helm et al. J Allergy Clin Immunol, 1996, 98: 172-180 |
| | Bla g 4 (a calycin) | Vailes et al. J Allergy Clin Immunol, 1998, 101: 274-280 |
| | Glutathione S-transferase | Arruda et al. J Biol Chem, 1997, 272: 20907-12 |
| | Per a 3 | Wu et al. Mol Immunol, 1997, 34: 1-8 |
| Dust mite | Der p 2 (major allergen) | Lynch et al. J Allergy Clin Immunol, 1998, 101: 562-4 Hakkaart et al. Clin Exp Allergy, 1998, 28: 169-74 Hakkaart et al. Clin Exp Allergy, 1998, 28: 45-52 Hakkaart et al. Int Arch Allergy Immunol, 1998, 115 (2): 150-6 Mueller et al. J Biol Chem, 1997, 272: 26893-8 |
| | Der p2 variant | Smith et al. J Allergy Clin Immunol, 1998, 101: 423-5 |
| | Der f2 | Yasue et al. Clin Exp Immunol, 1998, 113: 1-9 Yasue et al. Cell Immunol, 1997, 181: 30-7 |
| | Der p10 | Asturias et al. Biochim Biophys Acta, 1998, 1397: 27-30 |

TABLE 1-continued

RECOMBINANT ALLERGENS

| Group | Allergen | Reference |
|---|---|---|
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303-13 |
| Mosquito | Aed a I (salivary apyrase) | Xu et al. Int Arch Allergy Immunol, 1998, 115: 245-51 |
| Yellow jacket | antigen 5, hyaluronidase and phospholipase (venom) | King et al. J Allergy Clin Immunol, 1996, 98: 588-600 |
| MAMMALS | | |
| Cat | Fel d I | Slunt et al. J Allergy Clin Immunol, 1995, 95: 1221-8 Hoffmann et al. (1997) J Allergy Clin Immunol 99: 227-32 Hedlin Curr Opin Pediatr, 1995, 7: 676-82 |
| Cow | Bos d 2 (dander; a lipocalin) | Zeiler et al. J Allergy Clin Immunol, 1997, 100: 721-7 Rautiainen et al. Biochem Bioph. Res Comm., 1998, 247: 746-50 |
| | β-lactoglobulin (BLG, major cow milk allergen) | Chatel et al. Mol Immunol, 1996, 33: 1113-8 Lehrer et al. Crit Rev Food Sci Nutr, 1996, 36: 553-64 |
| Dog | Can f I and Can f 2, salivary lipocalins | Konieczny et al. Immunology, 1997, 92: 577-86 Spitzauer et al. J Allergy Clin Immunol, 1994, 93: 614-27 Vrtala et al. J Immunol, 1998, 160: 6137-44 |
| Horse | Equ c1 (major allergen, a lipocalin) | Gregoire et al. J Biol Chem, 1996, 271: 32951-9 |
| Mouse | mouse urinary protein (MUP) | Konieczny et al. Immunology, 1997, 92: 577-86 |
| OTHER MAMMALIAN ALLERGENS | | |
| Insulin | | Ganz et al. J Allergy Clin Immunol, 1990, 86: 45-51 Grammer et al. J Lab Clin Med, 1987,109: 141-6 Gonzalo et al. Allergy, 1998, 53: 106-7 |
| Interferons | interferon alpha 2c | Detmar et al. Contact Dermatis, 1989, 20: 149-50 |
| MOLLUSCS | topomyosin | Leung et al. J Allergy Clin Immunol, 1996, 98: 954-61 |
| PLANT ALLERGENS: | | |
| Barley | Hor v 9 | Astwood et al. Adv Exp Med Biol, 1996, 409: 269-77 |
| Birch | pollen allergen, Bet v 4 | Twardosz et al. Biochem Bioph. Res Comm., 1997, 239: 197 |
| | rBet v 1 Bet v 2: (profilin) | Pauli et al. J Allergy Clin Immunol, 1996, 97: 1100-9 van Neerven et al. Clin Exp Allergy, 1998, 28: 423-33 Jahn-Schmid et al. Immunotechnology, 1996, 2: 103-13 Breitwieser et al. Biotechniques, 1996, 21: 918-25 Fuchs et al. J Allergy Clin Immunol, 1997, 100: 3 56-64 |
| Brazil nut | globulin | Bartolome et al. Allergol Immunopathol, 1997, 25: 135-44 |

TABLE 1-continued

RECOMBINANT ALLERGENS

| Group | Allergen | Reference |
|---|---|---|
| Cherry | Pru a I (major allergen) | Scheurer et al. Mol Immunol, 1997, 34: 619-29 |
| Corn | Zml3 (pollen) | Heiss et al. FEBS Lett, 1996, 381: 217-21 |
| | | Lehrer et al. Int Arch Allergy Immunol, 1997, 113: 122-4 |
| Grass | Phl p 1, Phl p 2, Phl p 5 (timothy grass pollen) | Bufe et al. Am J Respir Crit Care Med, 1998, 157: 1269-76 |
| | | Vrtala et al. J Immunol Jun. 15, 1998, 160: 6137-44 |
| | | Niederberger et al. J Allergy Clin Immun., 1998, 101: 258-64 |
| | Hol 1 5 velvet grass pollen | Schramm et al. Eur J Biochem, 1998, 252: 200-6 |
| | Bluegrass allergen | Zhang et al. J Immunol, 1993, 151: 791-9 |
| | Cyn d 7 Bermuda grass | Smith et al. Int Arch Allergy Immunol, 1997, 114: 265-71 |
| | Cyn d 12 (a profilin) | Asturias et al. Clin Exp Allergy, 1997, 27: 1307-13 |
| | | Fuchs et al. J Allergy Clin Immunol, 1997, 100: 356-64 |
| Japanese Cedar | Jun a 2 (*Juniperus ashei*) | Yokoyama et al. Biochem. Biophys. Res. Commun., 2000, 275: 195-202 |
| | Cry j 1, Cry j 2 (*Cryptomeria japonica*) | Kingetsu et al. Immunology, 2000, 99: 625-629 |
| Juniper | Jun o 2 (pollen) | Tinghino et al. J Allergy Clin Immunol, 1998, 101: 772-7 |
| Latex | Hev b 7 | Sowka et al. Eur J Biochem, 1998, 255: 213-9 |
| | | Fuchs et al. J Allergy Clin Immunol, 1997, 100: 3 56-64 |
| *Mercurialis* | Mer a I (profilin) | Vallverdu et al. J Allergy Clin Immunol, 1998, 101: 3 63-70 |
| Mustard (Yellow) | Sin a I (seed) | Gonzalez de la Pena et al. Biochem Bioph. Res Comm., 1993, 190: 648-53 |
| Oilseed rape | Bra r I pollen allergen | Smith et al. Int Arch Allergy Immunol, 1997, 114: 265-71 |
| Peanut | Ara h I | Stanley et al. Adv Exp Med Biol, 1996, 409: 213-6 |
| | | Burks et al. J Clin Invest, 1995, 96: 1715-21 |
| | | Burks et al. Int Arch Allergy Immunol, 1995, 107: 248-50 |
| *Poa pratensis* | Poa p9 | Parronchi et al. Eur J Immunol, 1996, 26: 697-703 |
| | | Astwood et al. Adv Exp Med Biol, 1996, 409: 269-77 |
| Ragweed | Amb a I | Sun et al. Biotechnology August 1995, 13: 779-86 |
| | | Hirschwehr et al. J Allergy Clin Immunol, 1998, 101: 196-206 |
| | | Casale et al. J Allergy Clin Immunol, 1997, 100: 110-21 |
| Rye | Lol p I | Tamborini et al. Eur J Biochem, 1997, 249: 886-94 |
| Walnut | Jug r I | Teuber et al. J Allergy Clin Immun., 1998, 101: 807-14 |
| Wheat | allergen | Fuchs et al. J Allergy Clin Immunol, 1997, 100: 356-64 |
| | | Donovan et al. Electrophoresis, 1993, 14: 917-22 |
| FUNGI: | | |
| *Aspergillus* | Asp f 1, Asp f 2, Asp f3, Asp f 4, rAsp f 6 | Crameri et al. Mycoses, 1998, 41 Suppl 1: 56-60 |
| | | Hemmann et al. Eur J Immunol, 1998, 28: 1155-60 |
| | | Banerjee et al. J Allergy Clin Immunol, 1997, 99: 821-7 |
| | | Crameri Int Arch Allergy Immunol, 1998, 115: 99-114 |
| | | Crameri et al. Adv Exp Med Biol, 1996, 409: 111-6 |
| | | Moser et al. J Allergy Clin Immunol, 1994, 93: 1-11 |
| *Blomia* | Manganese superoxide dismutase (MNSOD) allergen | Mayer et al. Int Arch Allergy Immunol, 1997, 113: 213-5 |
| | | Caraballo et al. Adv Exp Med Biol, 1996, 409: 81-3 |
| *Penicillinium* | allergen | Shen et al. Clin Exp Allergy, 1997, 27: 682-90 |
| *Psilocybe* | Psi c 2 | Horner et al. Int Arch Allergy Immunol, 1995, 107: 298-300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza, Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446-4450; Scherle and Gerhard (1986) *J. Exp. Med.* 164:1114-1128; Granoff et al. (1993) *Vaccine* 11:S46-51; Kodihalli et al. (1997) *J. Virol.* 71:3391-3396; Ahmeida et al. (1993) *Vaccine* 11:1302-1309; Chen et al. (1999) *Vaccine* 17:653-659; Govorkova and Smirnov (1997) *Acta Virol.* (1997) 41:251-257; Koide et al. (1995) *Vaccine* 13:3-5; Mbawuike et al. (1994) *Vaccine* 12:1340-1348; Tamura et al. (1994) *Vaccine* 12:310-316; Tamura et al. (1992) *Eur. J. Immunol.* 22:477-481; Hirabayashi et al. (1990) *Vaccine* 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Poliovirus Vaccine Inactivated, Pasteur Merieux Connaught) and ORIMUNE® (Oral Poliovirus Vaccine, Lederle Laboratories), hepatitis A virus as VAQTA® (Hepatitis A Vaccine, Inactivated, Merck), measles virus as ATTENUVAX® (Measles Virus Vaccine Live, Merck), mumps virus as MUMPSVAX® (Mumps Virus Vaccine Live, Merck) and rubella virus as MERUVAX®II (Rubella Virus Vaccine Live, Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362: 833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible in a yearly publication, see Human Retroviruses and AIDS Compendium (for example, 1998 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

IMP/MC complex formulations may be prepared with other immunotherapeutic agents including, but not limited to, cytokine, adjuvants and antibodies, such as anti-tumor antibodies and derivatives thereof. These IMP/MC complex formulations may be prepared with or without antigen.

IMP/MC Complexes

IMP/MC complexes comprise an IMP bound to the surface of, or inserted into, a microcarrier (i.e., the IMP is not encapsulated in the MC), and preferably comprise multiple molecules of IMP bound to each microcarrier. In certain embodiments, a mixture of different IMPs may be complexed with a microcarrier, such that the microcarrier is bound to more than one IMP species. The bond between the IMP and MC may be covalent or non-covalent. As will be understood by one of skill in the art, the IMP may be modified or derivatized and the composition of the microcarrier may be selected and/or modified to accommodate the desired type of binding desired for IMP/MC complex formation.

The instant invention provides methods of making IMP/MC complexes, as well as the products of such methods. IMP/MC complexes are made by combining an IMP and an MC to form a complex. The specific process for combining the IMP and MC to form a complex will, of course, depend on the type and features of the MC as well as the mode of conjugation of the IMP and MC. When the MC is a solid phase MC, the IMP/MC complex is preferably made by contacting the IMP and the MC under conditions which promote complex formation (which will depend on the type of linkage used in the complex). When the MC is liquid phase, the IMP may be combined with a preformed MC under conditions which promote complex formation or be combined with the components of the MC prior to formation of the MC. In the situation where the IMP is combined with the components of a liquid phase MC, the process of making the MC may incorporate the IMP, thus resulting in the simultaneous creation of IMP/MC complexes, or when it does not, the process will involve an additional step under conditions which promote complex formation.

IMP/MC complexes in accordance with the invention are insoluble in pure water, and IMP/MC complex compositions are preferably free of acetonitrile, dichloroethane, toluene, and methylene chloride (dichlormethane).

Covalently bonded IMP/MC complexes may be linked using any covalent crosslinking technology known in the art. Typically, the IMP portion will be modified, either to incorporate an additional moiety (e.g., a free amine, carboxyl or sulfhydryl group) or incorporate modified (e.g., phosphorothioate) nucleotide bases to provide a site at which the IMP portion may be linked to the microcarrier. The link between the IMP and MC portions of the complex can be made at the 3' or 5' end of the IMP, or at a suitably modified base at an internal position in the IMP. The microcarrier is generally also modified to incorporate moieties through which a covalent link may be formed, although functional groups normally present on the microcarrier may also be utilized. The IMP/MC is formed by incubating the IMP with a microcarrier under conditions which permit the formation of a covalent complex (e.g., in the presence of a crosslinking agent or by use of an activated microcarrier comprising an activated moiety which will form a covalent bond with the IMP).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IMP and the microcarrier as well as the desired final configuration of the IMP/MC complex. The crosslinker may be either homobifunctional or heterobifunctional. When a homobifunctional crosslinker is used, the crosslinker exploits the same moiety on the IMP and MC (e.g., an aldehyde crosslinker may be used to covalently link an IMP and MC where both the IMP and MC comprise one or more free amines). Heterobifunctional crosslinkers utilize different moieties on the the IMP and MC, (e.g., a maleimido-N-hydroxysuccinimide ester may be used to covalently link a free sulfhydryl on the IMP and a free amine on the MC), and are preferred to minimize formation of inter-microcarrier bonds. In most cases, it is preferable to crosslink through a first crosslinking moiety on the microcarrier and a second crosslinking moiety on the IMP, where the second crosslinking moiety is not present on the microcarrier. One preferred method of producing the IMP/MC complex is by 'activating' the microcarrier by incubating with a heterobifunctional crosslinking agent, then forming the IMP/MC complex by incubating the IMP and activated MC under conditions appropriate for reaction. The crosslinker may incorporate a "spacer" arm between the reactive moieties, or the two reactive moieties in the crosslinker may be directly linked.

In one preferred embodiment, the IMP portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IMP to form the IMP/MC complex.

Non-covalent IMP/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IMP and MC.

Preferred non-covalent IMP/MC complexes are typically complexed by hydrophobic or electrostatic (ionic) interactions, or a combination thereof, (e.g., through base pairing between an IMP and a polynucleotide bound to an MC use of a binding pair). Due to the hydrophilic nature of the backbone of polynucleotides, IMP/MC complexes which rely on hydrophobic interactions to form the complex generally require modification of the IMP portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the IMP will, of course, depend on the configuration of the IMP and the identity of the hydrophobic moiety. The hydrophobic moiety may be added at any convenient site in the IMP, preferably at either the 5' or 3' end; in the case of addition of a cholesterol moiety to an IMP, the cholesterol moiety is preferably added to the 5' end of the IMP, using conventional chemical reactions (see, for example, Godard et al. (1995) *Eur. J. Biochem.* 232:404-410). Preferably, microcarriers for use in IMP/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the IMP/MC complex is formed by mixing the IMP and the MC after preparation of the MC, in order to avoid encapsulation of the IMP during the MC preparation process.

Non-covalent IMP/MC complexes bound by electrostatic binding typically exploit the highly negative charge of the polynucleotide backbone. Accordingly, microcarriers for use in non-covalently bound IMP/MC complexes are generally positively charged (e.g., cationic) at physiological pH (e.g., about pH 6.8-7.4). The microcarrier may intrinsically possess a positive charge, but microcarriers made from compounds not normally possessing a positive charge may be derivatized or otherwise modified to become positively charged (e.g., cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles, as described, for example, in Example 5). Thus, microcarriers may comprise a positively charged moiety.

As described herein, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

As described herein, IMP/MC complexes can be preformed by adsorption onto cationic microspheres by incubation of IMP and the particles, preferably in an aqueous admixture. Such incubation may be carried out under any desired conditions, including ambient (room) temperature (e.g., approximately 20° C.) or under refrigeration (e.g., 4° C.). Because cationic microspheres and IMPs associate relatively quickly, the incubation may be for any convenient time period, such as 5, 10, 15 minutes or more, including overnight and longer incubations. For example, ISS-containing polynucleotides can be adsorbed onto the cationic microspheres by overnight aqueous incubation of ISS and the particles at 4° C. However, because cationic microspheres and oligonucleotides spontaneously associate, the IMP/MC complex can be formed by simple co-administration of the oligonucleotide and the MC. Microspheres may be characterized for size and surface charge before and after IMP association. Selected batches may then evaluated for activity against suitable controls in, for example, established human peripheral blood mononuclear cell (PBMC) and mouse splenocyte assays, as described herein. The formulations may also evaluated in suitable animal models.

Non-covalent IMP/MC complexes linked by nucleotide base pairing may be produced using conventional methodologies. Generally, base-paired IMP/MC complexes are produced using a microcarrier comprising a bound, preferably a covalently bound, polynucleotide (the "capture polynucleotide") that is at least partially complementary to the IMP. The segment of complementarity between the IMP and the capture nucleotide is preferably at least 6, 8, 10 or 15 contiguous base pairs, more preferably at least 20 contiguous base pairs. The capture nucleotide may be be bound to the MC by any method known in the art, and is preferably covalently bound to the IMP at the 5' or 3' end.

In other embodiments, a binding pair may be used to link the IMP and MC in an IMP/MC complex. The binding pair may be a receptor and ligand, an antibody and antigen (or epitope), or any other binding pair which binds at high affinity (e.g., $K_d$ less than about $10^{-8}$). One type of preferred binding pair is biotin and streptavidin or biotin and avidin, which form very tight complexes. When using a binding pair to mediate IMP/MC complex binding, the IMP is derivatized, typically by a covalent linkage, with one member of the binding pair, and the MC is derivatized with the other member of the binding pair. Mixture of the two derivatized compounds results in IMP/MC complex formation.

Many IMP/MC complex embodiments do not include an antigen, and certain embodiments exclude antigen(s) associated with the disease or disorder which is the object of the IMP/MC complex therapy. In further embodiments, the IMP is also bound to one or more antigen molecules. Antigen may be coupled with the IMP portion of an IMP/MC complex in a variety of ways, including covalent and/or non-covalent interactions, as described, for example, in WO 98/16247. Alternately, the antigen may be linked to the microcarrier (either directly or indirectly). Linkage of the antigen to the microcarrier can be accomplished by any of a large number of methods known in the art, including, but not limited to, direct covalent linkage, covalent conjugation via a crosslinker moiety (which may include a spacer arm), noncovalent conjugation via a specific binding pair (e.g., biotin and avidin), and noncovalent conjugation via electrostatic or hydrophobic bonding.

The link between the antigen and the IMP in IMP/MC complexes comprising an antigen bound to the IMP can be made at the 3' or 5' end of the IMP, or at a suitably modified base at an internal position in the IMP. If the antigen is a peptide and contains a suitable reactive group (e.g., an N-hydroxysuccinimide ester) it can be reacted directly with the $N^4$ amino group of cytosine residues. Depending on the number and location of cytosine residues in the IMP, specific coupling at one or more residues can be achieved.

Alternatively, modified nucleosides or nucleotides, such as are known in the art, can be incorporated at either terminus, or at internal positions in the IMP. These can contain blocked functional groups which, when deblocked, are reactive with a variety of functional groups which can be present on, or attached to, the antigen of interest.

Where the antigen is a peptide, this portion of the conjugate can be attached to the 3'-end of the IMP through solid support chemistry. For example, the IMP portion can be added to a polypeptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the IMP can be synthesized such that it is connected to a solid support through a cleavable linker extending from the 3'-end. Upon chemical cleavage of the IMP from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified IMP to amino groups of the peptide can be performed as described in Benoit et al. (1987) *Neuromethods* 6:43-72. Conjugation of the thiol-modified IMP to carboxyl groups of the peptide can be performed as described in Sinha et al. (1991), pp. 185-210, Oligonucleotide Analogues: A Practical Approach, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide portion of the conjugate can be attached to the 5'-end of the IMP through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinha et al. (1991).

An IMP-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an IMP and residues within the antigen, such as charged amino acids, or through the use of a linker portion comprising charged residues that can interact with both the oligonucleotide and the antigen. For example, non-covalent conjugation can occur between a generally negatively-charged ISS and positively-charged amino acid residues of a peptide, e.g., polylysine, polyarginine and polyhistidine residues.

Non-covalent conjugation between IMP and antigens can occur through DNA binding motifs of molecules that interact with DNA as their natural ligands. For example, such DNA binding motifs can be found in transcription factors and anti-DNA antibodies.

The linkage of the IMP to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the IMP to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular IMP to a peptide or antigen can be formed in several ways. Where the circular IMP is synthesized using recombinant or chemical methods, a modified nucleoside is suitable. Ruth (1991), pp. 255-282, in Oligonucleotides and Analogues: A Practical Approach, IRL Press. Standard linking technology can then be used to connect the circular IMP to the antigen or other peptide. Goodchild (1990) *Bioconjug. Chem.* 1:165. Where the circular IMP is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) Nonisotopic DNA Probe Techniques, Academic Press; and Geoghegan et al. (1992) *Bioconjug. Chem.* 3:138-146.

Methods of the Invention

The invention provides methods of modulating an immune response in an individual, preferably a mammal, more preferably a human, comprising administering to the individual an IMP/MC complex (typically in a composition comprising the complex and a pharmaceutically acceptable excipient) such that the desired modulation of the immune response is achieved. Immunomodulation may include stimulating a Th1-type immune response and/or inhibiting or reducing a Th2-type immune response. As described herein, modulation of an immune response may be humoral and/or cellular, and is measured using standard techniques in the art and as described herein.

In some embodiments, the immune modulation comprises stimulating a (i.e., one or more) Th1-associated cytokine, such as IFN-γ, IL-12 and/or IFN-α. In some embodiments, the immune modulation comprises suppressing production of a (i.e., one or more) Th2-associated cytokine, such as IL-4 and/or IL-5. Measuring these parameters uses methods standard in the art and has been discussed herein.

As described herein, administration of IMP/MC may further comprise administration of one or more additional immunotherapeutic agents (i.e., an agent which acts via the immune system and/or is derived from the immune system) including, but not limited to, cytokine, adjuvants and antibodies. Examples of therapeutic antibodies include those used in the cancer context (e.g., anti-tumor antibodies). Administration of such additional immunotherapeutic agents applies to all the methods described herein.

In certain embodiments, the individual suffers from a disorder associated with a Th2-type immune response, such as allergies or allergy-induced asthma. Administration of an IMP/MC complex results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer).

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., *M. tuberculosis* antigens as a vaccine for prevention of tuberculosis). Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients. The IMP/MC complex may be given in conjunction with the vaccine (e.g., in the same injection or a contemporaneous, but separate, injection) or the IMP/MC complex may be administered separately (e.g., at least 12 hours before or after administration of the vaccine). In certain embodiments, the antigen(s) of the vaccine is part of the IMP/MC complex, by either covalent or non-covalent linkage to the IMP/MC complex. Administration of IMP/MC complex therapy to an individual receiving a vaccine results in an immune response to the vaccine that is shifted towards a Th1-type response as compared to individuals which receive vaccine without IMP/MC complex. Shifting towards a Th1-type response may be recognized by a delayed-type hypersensitivity (DTH) response to the antigen(s) in the vaccine, increased IFN-γ and other Th1-type response associated cytokines, increased IFN-α, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of IMP/MC complex and vaccine also results in amelioration of the symptoms of the disorder which the vaccine is intended to treat. As will be apparent to one of skill in the art, the exact symptoms and manner of their improvement will depend on the disorder sought to be treated. For example, where the therapeutic vaccine is for tuberculosis, IMP/MC complex treatment with vaccine results in reduced coughing, pleural or chest wall pain, fever, and/or other symptoms known in the art. Where the vaccine is an allergen used in allergy desensitization therapy, the treatment results in a reduction in one or more symptoms of allergy (e.g., reduction in rhinitis, allergic conjunctivitis, circulating levels of IgE, and/or circulating levels of histamine).

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and a reduction in symptoms. Administration of an IMP/MC complex to an individual having cancer results in stimulation of a Th1-type immune response against the tumor cells. Such an immune response can kill tumor cells, either by direct action of cellular immune system cells (e.g., CTLs) or components of the humoral immune system, or by bystander effects on cells proximal to cells targeted by the immune system. In the cancer context, administration of IMP/MC complex may further comprise administration of one or more additional therapeutic agents such as, for example, anti-tumor antibodies, chemotherapy regimens and/or radiation treatments. Anti-tumor antibodies, including, but not limited to anti-tumor antibody fragments and/or derivatives thereof, and monoclonal anti-tumor antibodies, fragments and/or derivatives thereof, are known in the art as is administration of such antibody reagents in cancer therapy (e.g., RITUXAN® (rituximab); HERCEPTIN® (trastuzumab)). Administration of one or more additional therapeutic agents may occur before, after and/or concurrent with administration of the IMP/MC complexes.

Immunomodulatory therapy in accordance with the invention is also useful for individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). IMP/MC complex therapy may be administered to individuals suffering from mycobacterial diseases such as tuberculosis (e.g., *M. tuberculosis* and/or *M. bovis* infections), leprosy (i.e., *M. leprae* infections), or *M. marinum* or *M. ulcerans* infections. IMP/MC complex therapy is also useful for the treatment of viral infections, including infections by influenza virus, respiratory syncytial virus (RSV), hepatitis virus B, hepatitis virus C, herpes viruses, particularly herpes simplex viruses, and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi*, and/or *L. aethiopica*), and toxoplasmosis (i.e., infection by *Toxoplasmosis gondii*) also benefit from IMP/MC complex therapy. IMP/MC therapy is also useful for treatment of parasitic diseases such as schistosomiasis (i.e., infection by blood flukes of the genus *Schistosoma* such as *S. haematobium, S. mansoni, S. japonicum*, and *S. mekongi*) and clonorchiasis (i.e., infection by *Clonorchis sinensis*). Administration of an IMP/MC complex to an individual suffering from an infectious disease results in an amelioration of one or more symptoms of the infectious disease. As indicated herein, in some embodiments, the infectious disease is not a viral disease.

The invention further provides methods of increasing at least one Th1-associated cytokine in an individual, including IL-2, IL-12, TNF-β, and IFN-γ. In certain embodiments, the invention provides methods of increasing IFN-γ in an individual, particularly in an individual in need of increased IFN-γ levels, by administering an effective amount of an IMP/MC complex to the individual. Individuals in need of increased IFN-γ are those having disorders which respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. Administration of IMP/MC complex in accordance with the invention results in an increase in IFN-γ levels, and results in amelioration of one or more symptoms, stabilization of one or more symptoms, or prevention of progression (e.g., reduction or elimination of additional lesions or symptoms) of the disorder which responds to IFN-γ. The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing IFN-α in an individual, particularly in an individual in need of increased IFN-α levels, by administering an effective amount of an IMP/MC complex to the individual such that IFN-α levels are increased. Individuals in need of increased IFN-α are those having disorders which respond to the administration of IFN-α, including recombinant IFN-α, including, but not limited to, viral infections and cancer. Accordingly, administration of an IMP/MC complex in accordance with the invention results in an increase in IFN-α levels, and results in amelioration of one or more symptoms, stabilization of one or more symptoms, or prevention of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

Also provided are methods of reducing levels, particularly serum levels, of IgE in an individual having an IgE-related disorder by administering an effective amount of an IMP/MC complex to the individual such that levels of IgE are reduced. Reduction in IgE results in an amelioration of symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of a allergic response.

As will be apparent to one of skill in the art, the methods of the invention may be practiced in combination with other therapies for the particular indication for which the IMP/MC complex is administered. For example, IMP/MC complex therapy may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

Administration and Assessment of the Immune Response

The IMP/MC complex can be administered in combination with other pharmaceutical and/or immunogenic and/or immunostimulatory agents and can be combined with a physiologically acceptable carrier thereof.

Accordingly, the IMP/MC complex can be administered in conjunction with other immunotherapeutic agents including, but not limited to, cytokine, adjuvants and antibodies.

The ISS-containing polynucleotide may be any of those described above. As indicated in SEQ ID NO:1, preferably, the ISS-containing polynucleotide administered comprises the sequence 5'-T, C, G-3'. Preferably, the ISS-containing polynucleotide administered comprises the formula 5' purine, purine, C, G, pyrimidine, pyrimidine, C, G-3'; more preferably, 5'-A, A, C, G, T, T, C, G-3'. Another preferred embodiment uses a polynucleotide comprising the sequence 5'-CG-3' and further comprising the sequence 5'-TCG-3'. Another preferred embodiment uses SEQ ID NO:1. Another preferred embodiment uses a polynucleotide comprising or, alternatively, consisting of the sequence selected from the group consisting of 5'-TCGX$_1$X$_2$X$_3$X$_4$-3', 5'-X$_1$TCGX$_2$X$_3$X$_4$-3' and 5'-X$_1$X$_2$TCGX$_3$X$_4$-3', wherein X$_1$, X$_2$, X$_3$, X$_4$ are nucleotides.

The IMP/MC complex may comprise any combination of the IMPs and MCs described above, so long as the IMP/MC is active. Generally, in some embodiments, an IMP/MC complex will be considered active if it has an activity (i.e., affects a measurable immune response as measured in vitro, in vivo and/or ex vivo) of at least about two times, preferably at least about three times, more preferably at least about five times, even more preferably at least about ten times the activity of a negative control in at least one assay of activity. Methods of assessing a measurable immune response are well known in the art, and include the human PBMC assay disclosed herein.

As with all immunogenic compositions, the immunologically effective amounts and method of administration of the particular IMP/MC complex formulation can vary based on the individual, what condition is to be treated and other factors evident to one skilled in the art. Factors to be considered include the antigenicity, whether or not the IMP/MC complex will be administered with or covalently attached to an adjuvant or delivery molecule, route of administration and the number of immunizing doses to be administered. Such factors are known in the art and it is well within the skill of those in the art to make such determinations without undue experimentation. A suitable dosage range is one that provides the desired modulation of immune response to the antigen. Generally, dosage is determined by the amount of IMP administered to the patient, rather than the overall quantity of IMP/MC complex. Useful dosage ranges of the IMP/MC complex, given in amounts of IMP delivered, may be, for example, from about any of the following: 0.1 to 100 µg/kg, 0.1 to 50 µg/kg, 0.1 to 25 µg/kg, 0.1 to 10 µg/kg, 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 25 µg, 50 µg and 100 µg. The absolute amount given to each patient depends on pharmacological properties such as bioavailability, clearance rate and route of administration.

The effective amount and method of administration of the particular IMP/MC complex formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient ISS-containing composition to attain a tissue concentration of about 1-10 µM as measured by blood levels. The absolute amount given to each patient depends on pharmacological properties such as bioavailability, clearance rate and route of administration.

As described herein, APCs and tissues with high concentration of APCs are preferred targets for the IMP/MC complexes. Thus, administration of IMP/MC complex to mammalian skin and/or mucosa, where APCs are present in relatively high concentration, is preferred.

The present invention provides IMP/MC complex formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein an IMP/MC complex are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the IMP/MC complex to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LECTRO PATCH product; those instructions are incorporated herein by this reference. Other occlusive patch systems are also suitable.

For transdermal transmission, low-frequency ultrasonic delivery is also a suitable method. Mitragotri et al. (1995) *Science* 269:850-853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up IMP/MC complex transferred from the end of the tines. For example, the MONO-VACC old tuberculin test manufactured by Pasteur Merieux of Lyon, France contains a device suitable for introduction of IMP/MC complex-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of IMP/MC complex formulation. Use of the device is preferably according to the manufacturer's written instructions included with the device product. Similar devices which can also be used in this embodiment are those which are currently used to perform allergy tests.

Another suitable approach to epidermal administration of IMP/MC complex is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The IMP/MC complex can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. IMP/MC formulations suitable for parenteral administration are generally formulated in USP water or water for injection and may further comprise pH buffers, salts bulking agents, preservatives, and other pharmaceutically acceptable excipients. IMP/MC complexes for parenteral injection may be formulated in pharmaceutically acceptable sterile isotonic solutions such as saline and phosphate buffered saline for injection.

Gastrointestinal routes of administration include, but are not limited to, ingestion and rectal. The invention includes IMP/MC complex formulations suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes IMP/MC complex formulations suitable for administration by inhalation including, but not limited to, liquid suspensions for forming aerosols as well as powder forms for dry powder inhalation delivery systems. Devices suitable for administration by inhalation of IMP/MC complex formulations include, but are not limited to, atomizers, vaporizers, nebulizers, and dry powder inhalation delivery devices.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119-6125. Thus, one skilled in the art can take advantage of slight differences in immunogenicity elicited by different routes of administering the immunomodulatory oligonucleotides of the present invention.

The above-mentioned compositions and methods of administration are meant to describe but not limit the methods of administering the IMP/MC complex formulations of the invention. The methods of producing the various compositions and devices are within the ability of one skilled in the art and are not described in detail here.

Analysis (both qualitative and quantitative) of the immune response to IMP/MC complex formulations can be by any method known in the art, including, but not limited to, measuring antigen-specific antibody production (including measuring specific antibody subclasses), activation of specific populations of lymphocytes such as CD4+ T cells or NK cells, production of cytokines such as IFN-γ, IFN-α, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Cytotoxicity assays can be performed for instance as described in Raz et al. (1994) *Proc. Natl. Acad. Sci. USA* 91:9519-9523. Cytokine concentrations can be measured, for example, by ELISA. These and other assays to evaluate the immune response to an immunogen are well known in the art. See, for example, Selected Methods in Cellular Immunology (1980) Mishell and Shiigi, eds., W.H. Freeman and Co.

Preferably, a Th1-type response is stimulated, i.e., elicited and/or enhanced. With reference to the invention, stimulating a Th1-type immune response can be determined in vitro or ex vivo by measuring cytokine production from cells treated with ISS as compared to those treated without ISS. Methods to determine the cytokine production of cells include those methods described herein and any known in the art. The type of cytokines produced in response to ISS treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, and IL-13. Cells useful for the determination of ISS activity include cells of the immune system, primary cells isolated from a host and/or cell lines, preferably APCs and lymphocytes, even more preferably macrophages and T cells.

Stimulating a Th1-type immune response can also be measured in a host treated with an IMP/MC complex formulation can be determined by any method known in the art including, but not limited to: (1) a reduction in levels of IL-4 or IL-5 measured before and after antigen-challenge; or detection of lower (or even absent) levels of IL-4 or IL-5 in an IMP/MC complex treated host as compared to an antigen-primed, or primed and challenged, control treated without ISS; (2) an increase in levels of IL-12, IL-18 and/or IFN (α, β or γ) before and after antigen challenge; or detection of higher levels of IL-12, IL-18 and/or IFN (α, β or γ) in an IMP/MC complex treated host as compared to an antigen-primed or, primed and challenged, control treated without ISS; (3) "Th1-type biased" antibody production in an IMP/MC complex treated host as compared to a control treated without ISS; and/or (4) a reduction in levels of antigen-specific IgE as measured before and after antigen challenge; or detection of lower (or even absent) levels of antigen-specific IgE in an IMP/MC complex treated host as compared to an antigen-primed, or primed and challenged, control treated without ISS. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to IMP/MC complex treatment indicate a Th1-type or a Th2-type biased immune response by the cells. As used herein, the term "Th1-type biased" antibody production refers to the measurable increased production of antibodies associated with a Th1-type immune response (i.e., Th1-associated antibodies). One or more Th1 associated antibodies may be measured. Examples of such Th1-type biased antibodies include, but are not limited to, human IgG1 and/or IgG3 (see, e.g., Widhe et al. (1998) *Scand. J. Immunol.* 47:575-581 and de Martino et al. (1999) *Ann. Allergy Asthma Immunol.* 83:160-164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of IMP/MC complex administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed. Suppression of a Th2 response may be determined by, for example, reduction in levels of Th2-associated cytokines, such as IL-4 and IL-5, as well as IgE reduction and reduction in histamine release in response to allergen.

Kits of the Invention

The invention provides kits for use in the methods of the invention. In certain embodiments, the kits of the invention comprise one or more containers comprising an IMP/MC complex and, optionally, a set of instructions, generally written instructions, relating to the use of the IMP/MC complex for the intended treatment (e.g., immunomodulation, ameliorating one or more symptoms of an infectious disease, increasing IFN-γ levels, increasing IFN-α levels, or ameliorating an IgE-related disorder). In further embodiments, the kits of the invention comprise containers of materials for producing IMP/MC, instructions for producing IMP/MC complex, and, optionally, instructions relating to the use of the IMP/MC complex for the intended treatment.

Kits which comprise preformed IMP/MC complex comprise IMP/MC complex packaged in any convenient, appropriate packaging. For example, if the IMP/MC complex is a dry formulation (e.g., freeze dried or a dry powder), a vial with a resilient stopper is normally used, so that the IMP/MC complex may be easily resuspended by injecting fluid through the resilient stopper. Ampoules with non-resilient, removable closures (e.g., sealed glass) or resilient stoppers are most conveniently used for liquid formulations of IMP/MC complex. Also contemplated are packages for use in combination with a specific device, such as an inhaler, nasal administration device (e.g., an atomizer) or an infusion device such as a minipump.

Kits which comprise materials for production of IMP/MC complex generally include separate containers of IMP and and MC, although in certain embodiments materials for producing the MC are supplied rather than preformed MC. The IMP and MC are preferably supplied in a form which allows formation of IMP/MC complex upon mixing of the supplied IMP and MC. This configuration is preferred when the IMP/MC complex is linked by non-covalent bonding. This configuration is also preferred when the IMP and MC are to be crosslinked via a heterobifunctional crosslinker; either IMP or the MC is supplied in an "activated" form (e.g., linked to the heterobifunctional crosslinker such that a moiety reactive with the IMP is available).

Kits for IMP/MC complexes comprising a solid phase MC preferably comprise one or more containers including materials for producing solid phase MC. For example, an IMP/MC kit for cationic MC may comprise one or more containers containing a polymer and a positively charged surfactant. The contents of the container are mixed, for example by emulsification, to produce the cationic MC, which may be then mixed with the IMP. Such materials include poly(lactic acid)/poly(glycolic acid) copolymers, containers of cationic lipid, for example, DOTAP, plus one or more containers of an aqueous phase (e.g., a pharmaceutically-acceptable aqueous buffer).

Kits for IMP/MC complexes comprising a liquid phase MC preferably comprise one or more containers including materials for producing liquid phase MC. For example, an IMP/MC kit for oil-in-water emulsion MC may comprise one or more containers containing an oil phase and an aqueous phase. The contents of the container are emulsified to produce the MC, which may be then mixed with the IMP, preferably an IMP which has been modified to incorporate a hydrophobic moiety. Such materials include oil and water, for production of oil-in-water emulsions, or containers of lyophilized liposome components (e.g., a mixture of phospholipid, cholesterol and a surfactant) plus one or more containers of an aqueous phase (e.g., a pharmaceutically-acceptable aqueous buffer).

The instructions relating to the use of IMP/MC complex for the intended treatment generally include information as to dosage, dosing schedule, and route of administration for the intended treatment. The containers of ISS may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The following Examples are provided to illustrate, but not limit, the invention.

EXAMPLES

Example 1

Production of Non-Covalent, Liquid Phase IMP/MC Complexes

IMP/MC complex comprising a modified IMP and a liquid phase MC were produced and tested for complex formation.

An IMP (phosphorothioate oligodeoxynucleotide 5'-TGACTGTGAACGTTCGAGATGA-3') (SEQ ID NO:1) was modified by addition of a cholesterol molecule to the 5' end of the IMP using phosphoramidite chemistry. An oil-in-water emulsion was produced by homogenization of a mixture of 4.5% (w/v) squalene, 0.5% (w/v) sorbitan trioleate, 0.5% (w/v) TWEEN® 80 (Polysorbate 80, Sigma-Aldrich) and 10 mM sodium citrate, pH 6.5, using a microfluidizer. Examination of the emulsion found that the oil droplets in the emulsion had an average diameter of approximately 160 nm.

The emulsion was mixed with the cholesterol-modified IMP or an unmodified version of the same IMP, then centrifuged to separate the oil and water phases. RP-HPLC was performed on samples from each phase to determine nucleotide content. Approximately 75% of the cholesterol-modified IMP was found in the oil phase, while 100% of the unmodified IMP was found in the aqueous phase.

Example 2

Immunomodulation with IMP/MC Mixtures

Mixtures of an IMP (phosphorothioate oligodeoxynucleotide 5'-TGACTGTGAACGTTCGAGATGA-3') (SEQ ID NO:1) or a control oligonucleotide (phosphorothioate oligodeoxynucleotide 5'-TGACTGTGAAGGTTAGAGATGA-3') (SEQ ID NO:9) were mixed with sulphate-derivatized polycarbonate microparticles or nanoparticles (Polysciences, Inc.) and assayed for immunomodulatory activity on mouse splenocytes.

Fragments of BALB/c mouse spleen were digested with collagenase/dispase (0.1 U/mL/0.8 U/mL) dissolved in phosphate buffered saline (PBS) for 45 minutes at 37° C., then mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol).

4×10$^5$ mouse splenocytes were dispensed into wells of 96 well plates and incubated for one hour at 37° C. 100 µL of 2× concentration test sample or control was added and the cells were incubated a further 24 hours. Medium was harvested from each well and tested for cytokine concentrations by ELISA.

IFN-γ was assayed using a sandwich-format ELISA. Medium from the mouse splenocyte assay was incubated in microtiter plates coated with anti-IFN-γ monoclonal antibody (Nunc). Bound IFN-γ was detected using a biotinylated anti-IFN-γ antibody and streptavidin-horseradish peroxidase conjugated secondary antibody, developed with the chromogenic peroxidase substrate 3,3',5,5'-tetramethylbenzidine (TMB) in the presence of peroxidase, and quantitated by measuring absorbance at 450 nm using a Emax precision microplate reader (Molecular Devices). IL-6 and IL-12 were assayed with the same method using anti-IL-6 antibody and anti-IL-12 antibody, respectively.

200 nm beads mixed with IMP substantially increased IL-12, IL-6 and IFN-γ secretion by mouse splenocytes, and 50 nm beads mixed with IMP increased IL-12 and IL-6 production. Some nonspecific activity was associated with 200 nm beads mixed with the control oligonucleotide, although this was insufficient to account for the increase in stimulation as compared to IMP alone. Additionally, microcarriers of 1 µm and 4.5 µm also increased cytokine secretion. Tables 2-4 summarize assay results for IL-12, IL-6 and IFN-γ, respectively.

TABLE 2

| Test Material | DNA dose | | |
|---|---|---|---|
| | 5 µg/ml | 1 µg/ml | 0.1 µg/ml |
| | IL-12 (pg/mL) | | |
| IMP | | | |
| alone | 6046 | 4737 | 915 |
| IMP + 50 nm | 8582 | 4934 | 364 |
| IMP + 200 nm | 7377 | 8393 | 984 |
| IMP + 500 nm | 3680 | 4260 | 833 |
| IMP + 1 µm | 5082 | 4652 | 613 |
| IMP + 4.5 µm | 2253 | 2306 | 838 |
| Control | | | |
| alone | 79 | 91 | 65 |
| control + 50 | 100 | 100 | 91 |
| control + 200 | 661 | 108 | 127 |
| control + 500 | 48 | 82 | 82 |
| control + 1000 | 72 | 101 | 147 |
| control + 4500 | 101 | 104 | 141 |

TABLE 3

| Test Material | DNA dose | |
|---|---|---|
| | 5 µg/ml | 0.1 µg/ml |
| | IL-6 (pg/mL) | |
| IMP | | |
| alone | 5290 | 1872 |
| IMP + 50 nm | >18000 | 2127 |
| IMP + 200 nm | 6946 | 3574 |
| IMP + 500 nm | 345 | 2133 |
| IMP + 1 µm | 3812 | 2107 |
| IMP + 4.5 µm | 3277 | 1846 |
| control | | |
| alone | 24 | 24 |
| control + 50 | 24 | 24 |

TABLE 3-continued

| Test Material | DNA dose | |
|---|---|---|
| | 5 µg/ml | 0.1 µg/ml |
| | IL-6 (pg/mL) | |
| control + 200 | 1842 | 232 |
| control + 500 | 24 | 24 |
| control + 1000 | 24 | 24 |
| control + 4500 | 30 | 24 |

TABLE 4

| Test Material | DNA dose | |
|---|---|---|
| | 5 µg/ml | 0.1 µg/ml |
| | IFN-γ (pg/mL) | |
| IMP | | |
| alone | 575 | 244 |
| IMP + 50 nm | 411 | 232 |
| IMP + 200 nm | 3548 | 3150 |
| IMP + 500 nm | 48 | 426 |
| IMP + 1 µm | 252 | 685 |
| IMP + 4.5 µm | 1072 | 2739 |
| control | | |
| alone | 48 | 48 |
| control + 50 | 48 | 48 |
| control + 200 | 1907 | 101 |
| control + 500 | 48 | 48 |
| control + 1000 | 48 | 48 |
| control + 4500 | 50 | 48 |

Example 3

Immunomodulation of Mouse Cells by IMP/NC Complexes

IMPs covalently linked to non-biodegradable polystyrene beads (200 nm design size) were tested for immunomodulatory activity on mouse splenocytes.

Phosphorothioate IMPs were synthesized with a disulfide linker on the 5'-end to facilitate linkage to the microcarrier. The C6 disulfide linker with a 4,4'-O-dimethoxytrityl group on one end and a cyanoethylphosphoramidite on the other end (Glen Research) was dissolved to a concentration of 0.1 M in acetonitrile. The linker was coupled to the 5'-end of the oligonucleotide and the resulting oligonucleotide was purified and isolated as described herein. The disulfide group on the oligonucleotide was reduced to a thiol before linkage to the microcarriers. The disulfide-oligonucleotide was dissolved to a concentration of 25 mg/ml in 100 mM sodium phosphate/150 mM sodium chloride/1 mM ethylenediamine tetraacetic acid (EDTA)/pH 7.5 buffer. Then 5 equivalents of the hydrochloride salt of tris(carboxyethyl)phosphine (TCEP; Pierce) were added and the solution was heated to 40° C. for 2 hours. The thiol-containing IMPs were purified from the small molecule by-products by size exclusion chromatography and either used immediately or stored at −80° C. until use.

Amine-derivatized polystyrene beads were obtained from Molecular Probes, Inc., and Polysciences, Inc. Three types of beads were utilized: amine-derivatized beads (Polysciences, Inc., Catalog No. 15699), amine-derivatized beads linked to a fluorophore with excitation/emission maxima of 580 and 605 nm ("Red Beads", Molecular Probes, Inc., Catalog No. F8763), and amine-derivatized beads linked to a fluorophore with excitation/emission maxima of 505 and 515 nm ("Yellow Beads", Molecular Probes, Inc., Catalog No. F8764) were activated with sulfo-SMCC (sulfosuccinimidyl 4-(N-maleimidomethyl)cyclopentane-1-carboxylate, Pierce Chemical Co.) according to the manufacturer's instructions. The beads were then linked to thiol-modified IMP (see Examples 1 and 2), a control phosphorothioate oligonucleotide (5'-TGACTGTGAAGGTTAGAGATGA-3' (control A) (SEQ ID NO:9), 5'-TGACTGTGAACCTTAGAGATGA-3' (control B) (SEQ ID NO:10), or 5'-TCACTCTCTTCCT-TACTCTTCT-3' (control C) (SEQ ID NO:11), or treated to quench the free maleimide group for use as a NC only control. The IMP/MC complexes were isolated by centrifugation and washed three time with phosphate buffered saline to remove excess oligonucleotide.

Immunomodulatory effects of the IMP/NC complexes were assayed using mouse splenocytes as described above in Example 2. IMP/NC complexes demonstrated immunomodulation on the mouse splenocytes, as shown by increased secretion of IL-12, IL-6 and/or IFN-γ, while control oligonucleotides complexed with NC did not stimulate cytokine secretion. Data for IFN-γ secretion is summarized in Table 5.

TABLE 5

| Sample | IFN-γ (pg/mL) | |
|---|---|---|
| | 5 μg/ml dose | 1 μg/ml dose |
| White Beads | | |
| NC alone | 48 | 48 |
| IMP/NC | 903 | 77 |
| Red Beads | | |
| NC alone | 48 | 48 |
| IMP/NC | 319 | 63 |
| control A/NC | 48 | 48 |
| control B/NC | 48 | 48 |
| sulfo-SMCC activated NC | 2869 | 2147 |
| Yellow Beads | | |
| NC alone-lot 7781-2 | 1224 | 147 |
| 145-57A: IMP/NC-lot 145-57A | 3437 | 2335 |
| 145-57B: IMP/NC-lot 145-57B | 4556 | 5497 |
| 145-146: IMP/NC-lot 145-146C | 11444 | 7091 |
| 135-171A: IMP/NC-135-171A | 4493 | 2359 |
| 135-171B: control A/NC | 147 | 147 |
| 145-148: control B/NC | 147 | 147 |
| sulfo-SMCC activated NC, BME-inactivated | 3163 | 3723 |
| sulfo-SMCC activated NC, cysteine inactivated | 3392 | 3090 |
| sulfo-SMCC activated NC | 3583 | 4108 |
| IMP Controls | | |
| IMP | 558 | 577 |
| control C | 48 | 48 |

Example 4

Immunomodulation of Human Cells by IMP/NC Complexes

IMPs covalently linked to non-biodegradable polystyrene beads (200 nm design size) were tested for immunomodulatory activity on human peripheral blood mononuclear cells (PBMCs).

Peripheral blood was collected from volunteers by venipuncture using heparinized syringes. Blood was layered onto FICOLL® (a centrifugal medium, Amersham Pharmacia Biotech) cushion and centrifuged. PBMCs, located at the FICOLL® interface, were collected, then washed twice with cold phosphate buffered saline (PBS). The cells were resuspended and cultured in 24 or 48 well plates at $2 \times 10^6$ cells/mL in RPMI 1640 with 10% heat-inactivated human AB serum plus 50 units/mL penicillin, 50 μg/mL streptomycin, 300 μg/mL glutamine, 1 mM sodium pyruvate, and 1×MEM non-essential amino acids (NEAA).

The cells were cultured in the presence of test samples (IMP/NC formulations or controls) for 24 hours, then cell-free medium was collected from each well and assayed for IFN-γ concentration. IFN-γ was assayed using a CYTO-SCREEN™ ELISA kit (an immunoassay kit from BioSource International, Inc., according to the manufacturer's instructions.

IMP/NC complexes stimulated IFN-γ secretion by human PBMCs. The results are summarized in Table 6.

TABLE 6

| | IFN-γ (pg/mL) | | | |
|---|---|---|---|---|
| | Experiment 1 | | Experiment 2 | |
| Sample | 5 μg/ml | 20 μg/ml | 5 μg/ml | 10 μg/ml |
| White Beads | | | | |
| NC alone | n/a | n/a | | |
| IMP/NC | 5 | 3 | | |
| Red Beads | | | | |
| NC alone | 2 | 8 | | |
| IMP/NC | 39 | 431 | | |
| control A/NC | 2 | 5 | | |
| control B/NC | 3 | 14 | | |
| sulfo-SMCC activated NC | 15 | n/a | | |
| Yellow Beads - Old | | | | |
| NC alone-lot 7781-2 | 12 | 56 | 8 | 19 |
| NC alone-lot 6991-1 | 7 | n/a | | |
| IMP/NC-lot 145-57A | 187 | n/a | | |
| IMP/NC-lot 145-57B | 777 | n/a | | |
| IMP/NC-lot 145-57C | 536 | 7752 | 6356 | 6413 |
| IMP/NC-lot 145-57D | 156 | 1861 | | |
| IMP/NC-lot 145-57E | 283 | 1385 | | |
| IMP/NC-lot 145-57F | 140 | n/a | | |
| IMP/NC-lot 145-146 | | | 934 | 6519 |
| IMP/NC-lot 135-171A | 123 | 2400 | | |
| control A/NC | 12 | 446 | | |
| control B/NC | | | 24 | 165 |
| sulfo-SMCC activated NC, BME-inactivated | | | 4 | 8 |
| sulfo-SMCC activated NC, cysteine inactivated | | | 7 | 15 |
| sulfo-SMCC activated NC | | | 7 | 14 |
| IMP Controls | | | | |
| IMP | <10 | <10 | | |

Example 5

Preparation of Biodegradable, Cationic Microspheres

Cationic poly(lactic acid, glycolic acid) (PLGA) microspheres were prepared as follows. 0.875 g of poly(D,L-lactide-co-glycolide) 50:50 polymer with an intrinsic viscosity of 0.41 dl/g (0.1%, chloroform, 25° C.) was dissolved in 7.875 g of methylene chloride at 10% w/w concentration, along with 0.3 g of DOTAP. The clear organic phase was then emulsified into 500 ml of PVA aqueous solution (0.35% w/v) by homogenization at 4000 rpm for 30 minutes at room temperature using a laboratory mixer (Silverson L4R, Silverson Instruments). System temperature was then raised to 40° C.

by circulating hot water through the jacket of the mixing vessel. Simultaneously, the stirring rate was reduced to 1500 rpm, and these conditions were maintained for 2 hours to extract and evaporate methylene chloride. The microsphere suspension was allowed to cool down to room temperature with the help of circulating cold water.

Microparticles were separated by centrifugation at 8000 rpm for 10 minutes at room temperature (Beckman Instruments) and resuspended in deionized water by gentle bath sonication. Centrifugal wash was repeated two additional times to remove excess PVA from particle surface. Final centrifugal pellets of particles are suspended in approximately 10 ml of water, and lyophilized overnight. Dried cationic microsphere powder was characterized for size and surface charge: mean size (number weighted, μ)=1.4; zeta potential (mV)=32.4.

200 mg of cationic microspheres from the above batch was dispersed in 1.875 ml of 0.1% w/v Tween solution by bath sonication for 5 minutes. 0.75 ml of aqueous ISS solution (SEQ ID NO:1) was added to the microsphere suspension to yield an approximate and theoretical drug loading of 2% w/w (ISS to microsphere). After a brief mixing, the ISS-microsphere suspension was incubated at 4° C. overnight. Microspheres were separated by centrifugation at 14,000 rpm for 30 minutes at room temperature in an Eppendorf centrifuge. The supernatant and the microspheres were assayed for free and bound ISS, respectively, by the standard laboratory analytical techniques to determine ISS association efficiency or loading. Adsorption of oligonucleotide to the microspheres was confirmed by determining loss of oligonucleotide from the aqueous supernatant using absorbance at 260 nm after centrifugation of the ISS-microsphere suspension. After ISS association, the preparation was also characterized for size and surface charge: mean size (number weighted, μ)=1.6; zeta potential (mV)=33.3; % ISS association (drug loading)=88 (1.78% w/w).

Example 6

Immunomodulatory Effects of IMP/MC Formulations

Preparations of cationic microspheres with and without adsorbed ISS were evaluated for immunomodulatory effects in a standard mouse splenocyte assay. Cationic microspheres were prepared as described in Example 5, with the exception that 0.2 g of DOTAP was used. Three doses of adsorbed ISS SEQ ID NO:1, 0.1, 1.0 and 5 μg/ml, were evaluated against the same doses of free ISS solution and blank (no drug) microspheres. The splenocyte assays were performed as described in Example 2 and results of these experiments are presented in Table 7.

At lower doses tested, IMP/MC formulations were more effective than free IMP at inducing IL-6, IL-12 and IFN-γ in the mouse splenocyte assay.

TABLE 7

| Sample | IL-6 (pg/mL) | IL-12 (pg/mL) | IFN-γ (pg/mL) |
| --- | --- | --- | --- |
| IMP | | | |
| 0.1 μg/ml | 27 | 368 | 9 |
| 1.0 μg/ml | 909 | 1694 | 273 |
| 5.0 μg/ml | 3340 | 1807 | 435 |

TABLE 7-continued

| Sample | IL-6 (pg/mL) | IL-12 (pg/mL) | IFN-γ (pg/mL) |
| --- | --- | --- | --- |
| IMP/MC | | | |
| 0.1 μg/ml | 114 | 1390 | 161 |
| 1.0 μg/ml | 226 | 1086 | 200 |
| 5.0 μg/ml | 850 | 540 | 200 |
| MC alone | | | |
| (0.1 μg/ml) | 27 | 27 | 9 |
| (1.0 μg/ml) | 31 | 27 | 9 |
| (5.0 μg/ml) | 27 | 84 | 9 |

Preparations of cationic microspheres with and without adsorbed IMP SEQ ID NO:1 were evaluated for immunomodulatory effects in a human PBMC assay. Cationic microspheres that were made as described in Example 5. Included as controls were (i) free IMP and (ii) a mixture of IMP and cationic microspheres. With IMP/MC formulations, IMP doses of 2 and 10 μml were used. The PBMC assays were performed as described in Example 4. IFN-γ and IFN-α were assayed using CYTOSCREEN™ ELISA kits (an immunoassay kit from BioSource International, Inc., according to the manufacturer's instructions.

In the human PMBC assay, background levels of IFN-γ can vary, even significantly, with the donor. Levels of IFN-α, however, demonstrate a generally stable pattern of activation and routinely exhibit low background levels under unstimulated conditions.

Results are shown in picograms per milliliter (pg/ml) of interferon-gamma (IFN-γ) or interferon-alpha (IFN-α). Because of variability between assays using different human donors, results are shown for assays using different donor cells (each value in the parentheses) and as a mean.

Results of such an experiment are presented in Table 8. The IMP/MC formulations were more active than free ISS in inducing IFN-α and were comparable to free ISS in inducing IFN-γ in the human PBMC assay. Each value in the table represents the mean of the two readings in parentheses.

TABLE 8

| Sample | IFN-γ (pg/mL) | IFN-α (pg/mL) |
| --- | --- | --- |
| IMP (10 μg/ml) | 63 (0, 127) | 0 (0, 0) |
| IMP + Microspheres mixture (IMP at 10 μg/ml) | 197 (82, 311) | 433 (175, 690) |
| IMP/MC | | |
| 2.0 μg/ml | 81 (61, 102) | 2584 (2247, 2921) |
| 10 μg/ml | 45 (10, 79) | 1866 (971, 2762) |

Example 7

Synthesis of 7-mer Oligonucleotides

The 7-mer oligonucleotide with the sequence 5'-TCGTCGA-3' (SEQ ID NO:12) with phosphorothioate linkages, was synthesized on a Perceptive Biosystems Expedite 8909 automated DNA synthesizer. The manufacturer's protocol for 15 μmol phosphorothioate DNA was used with the following changes: 1.6 ml of 3% dichloroacetic acid in dichloromethane over 2.5 minutes was used for the detrytilation step; and 3.0 ml of 0.02 M 3-amino-1,2,4-dithiazole-5-thione (ADTT) in 9:1 acetonitrile:pyridine over 1.1 minutes followed by a 1.0 ml delivery over 1.0 minutes was used for the sulfurization step. The nucleoside phosphoramidite monomers were dissolved in anhydrous acetonitrile to a concentration of 0.1 M. The instrument was programmed to add the nucleotide monomers in the desired order, with the synthesis occurring in the 3' to 5' direction. The synthesis cycle consisted of a detritylation step, a coupling step (phosphoramidite monomer plus 1H-tetrazole), a capping step, a sulfurization step, and a final capping step.

At the completion of the assembly, the 'trityl-on' oligonucleotide was cleaved from the controlled-pore glass and the bases were deprotected with concentrated aqueous ammonia at 58° C. for 16 hours.

The 7-mer oligonucleotide was purified by RP-HPLC on a Polymer Labs PLRP-S column using an increasing gradient of acetonitrile in 0.1 M triethylammonium acetate. The purified oligonucleotide was concentrated to dryness, the 4,4'-dimethoxytrityl group was removed with 80% aqueous acetic acid, and then the compound was precipitated two times from 0.6 M aqueous sodium acetate/pH 5.0 with 3 volumes of isopropanol. The 7-mer oligonucleotide was dissolved in Milli Q water and the yield was determined from the absorbance at 260 nm. Finally, the oligonucleotide was lyophilized to a powder.

The 7-mer oligonucleotide was characterized by capillary gel electrophoresis, electrospray mass spectrometry, and RP-HPLC to confirm composition and purity. An endotoxin content assay (LAL assay, Bio Whittaker) was also conducted, showing endotoxin levels were <5 EU/mg oligonucleotide.

Other 7-mer phosphorothioate oligonucleotides were synthesized using the same methods.

The 7-mer phosphorothioate oligonucleotide with the sequence 5'-TCGTCGA-3' (SEQ ID NO:12) was also synthesized with a disulfide linker on the 5'-end to facilitate linkage to the microcarrier. The C6 disulfide linker with a 4,4'-O-dimethoxytrityl group on one end and a cyanoethylphosphoramidite on the other end (Glen Research) was dissolved to a concentration of 0.1 M in acetonitrile. The linker was coupled to the 5'-end of the oligonucleotide and the resulting oligonucleotide was purified and isolated as described above.

The disulfide group on the oligonucleotide was reduced to a thiol before linkage to the microcarriers. The disulfide-oligonucleotide was dissolved to a concentration of 25 mg/ml in 100 mM sodium phosphate/150 mM sodium chloride/1 mM ethylenediamine tetraacetic acid (EDTA)/pH 7.5 buffer. Then 5 equivalents of the hydrochloride salt of tris(carboxyethyl)phosphine (TCEP; Pierce) were added and the solution was heated to 40° C. for 2 hours. The thiol-containing oligonucleotide was purified from the small molecule by-products by size exclusion chromatography and either used immediately or stored at −80° C. until use.

Example 8

Preparation of Unmodified Biodegradable Microspheres

Unmodified PLGA biodegradable microspheres were synthesized as described in Example 5, except the 0.3 g of DOTAP was omitted. The dried microsphere powder was characterized for size and surface charge: mean size (number weighted, =1.1; zeta potential (mV)=−18.1.

Example 9

Immunomodulation with IMP/MC Complexes in Human Cells

Heptameric oligonucleotides were tested for immunomodulatory activity alone and complexed with PLGA microspheres in the human PBMC assay. The human PBMC assay was performed as described in Example 4. Cationic and unmodified PLGA microspheres were prepared as described in Examples 5 and 8, respectively.

Oligonucleotides were tested as single agents, or in combination with PLGA microspheres (unmodified or cationic). The 7-mer oligonucleotides tested were 5'-TCGTCGA-3' (SEQ ID NO:12), 5'-ACGTTCG-3' (SEQ ID NO:13), 5'-ATCTCGA-3' (SEQ ID NO:14), and 5'-AGATGAT-3' (SEQ ID NO:15) (control). All oligonucleotides contained 100% phosphorothioate linkages and were tested at 20 µg/ml. The PLGA was added at a concentration of 250 µg/ml. When the oligonucleotides were tested with PLGA, the oligonucleotide and PLGA were added at the same time to the culture. SAC (PANSORBIN™ (*Staphylococcus aureus* cells, CalBiochem, 1/5000 dilution) and IMP, SEQ ID NO: 1, were used as positive controls, and control oligonucleotide, SEQ ID NO:10, and cells alone were used as negative controls. Unmodified microcarriers (unm MC) and cationic microcarriers (cat MC) were also tested alone. SAC contains *Staph. Aureus* (Cowan I) cell material. Samples were assayed in two healthy donors in duplicate.

As shown in Table 9 below, when used alone, the PLGA microspheres (cationic or unmodified) and the heptameric oligonucleotides had little activity, if any. However heptameric oligonucleotide, SEQ ID NO:12, was active in inducing IFN-α and IFN-γ in combination with cationic PLGA microspheres. Cationic PLGA adsorbs oligonucleotides by electrostatic bonding, creating an oligonucleotide/microcarrier complex, while unmodified PLGA does not. Each value in the table represents the mean of the two readings in parentheses.

TABLE 9

| Sample | IFN-γ (pg/mL) | IFN-α (pg/mL) |
| --- | --- | --- |
| SEQ ID NO: 1 | 161 (99, 223) | 67 (28, 106) |
| SEQ ID NO: 10 | 5 (3, 8) | 15 (0, 31) |
| SEQ ID NO: 12 | 2 (1, 4) | 16 (0, 32) |
| SEQ ID NO: 13 | 2 (3, 1) | 16 (0, 32) |
| SEQ ID NO: 14 | 2 (0, 3) | 29 (0, 57) |
| SEQ ID NO: 15 | 1 (0, 3) | 29 (0, 58) |
| unm MC | 7 (4, 10) | 154 (0, 308) |
| SEQ ID NO: 1 + unm MC | 90 (38, 143) | 115 (31, 199) |
| SEQ ID NO: 10 + unm MC | 15 (18, 13) | 16 (0, 32) |
| SEQ ID NO: 12 + unm MC | 74 (16, 132) | 499 (10, 988) |
| SEQ ID NO: 13 + unm MC | 7 (6, 8) | 14 (0, 28) |
| SEQ ID NO: 14 + unm MC | 8 (4, 12) | 16 (0, 32) |
| SEQ ID NO: 15 + unm MC | 8 (6, 10) | 15 (0, 31) |
| cat MC | 10 (13, 6) | 28 (6, 50) |
| SEQ ID NO: 1/cat MC | 398 (399, 397) | 1748 (2000, 1496) |
| SEQ ID NO: 10/cat MC | 9 (9, 10) | 11 (0, 21) |
| SEQ ID NO: 12/cat MC | 598 (454, 741) | 832 (553, 1111) |
| SEQ ID NO: 13/cat MC | 26 (15, 37) | 97 (0, 193) |
| SEQ ID NO: 14/cat MC | 7 (7, 8) | 41 (0, 82) |
| SEQ ID NO: 15/cat MC | 10 (16, 5) | 20 (0, 40) |
| SAC | 1589 (1179, 2000) | 510 (50, 969) |
| cells alone | 2 (0, 3) | 9 (0, 18) |

Table 10 below shows that the 7-mer oligonucleotide, SEQ ID NO:12, was active in two more healthy human donors when used with cationic microspheres. In this case the oligonucleotides and cationic microspheres were pre-mixed for 15 minutes at room temperature before they were added to the culture. Each value in the table represents the mean of the two readings in parentheses.

TABLE 10

| Sample | IFN-γ (pg/mL) | IFN-α (pg/mL) |
| --- | --- | --- |
| SEQ ID NO: 1 | 1425 (2180, 669) | 220 (401, 39) |
| SEQ ID NO: 10 | 231 (410, 51) | 0 (0, 0) |
| SEQ ID NO: 12 | 4 (8, 0) | 0 (0, 0) |
| cat MC | 97 (46, 148) | 1 (2, 0) |
| SEQ ID NO: 1/cat MC | 1925 (3382, 468) | 379 (587, 171) |
| SEQ ID NO: 10/cat MC | 131 (147, 115) | 0 (0, 0) |
| SEQ ID NO: 12/cat MC | 2294 (3575, 1012) | 5836 (9742, 1930) |
| SAC | 1588 (2040, 1136) | 218 (393, 43) |
| cells alone | 4 (8, 0) | 0 (0, 0) |

Example 10

Immunomodulation with IMP/MC Complexes

Heptameric oligonucleotides were tested for immunomodulatory activity alone and complexed with cationic PLGA microspheres under two different conditions in the human PBMC assay. The human PBMC assay was performed as described in Example 4. Cationic PLGA microspheres were prepared as described in Example 5.

Oligonucleotides were tested as single agents, in combination with other oligonucleotides, or in combination with cationic PLGA microspheres. The oligonucleotide and microsphere concentrations were 20 μg/ml and 250 μg/ml, respectively. When the oligonucleotides were tested with the cationic PLGA microspheres, the oligonucleotide and microspheres were added at the same time to the culture (simultaneously, see "simult. added" in Tables 12 and 13). When multiple oligonucleotides were tested in combination, equal weights of each oligonucleotide were pre-mixed and a total concentration of 20 μg/ml was used. The oligonucleotides were also complexed with the cationic PLGA microspheres under the conditions described in Example 5 in order to obtain a 2% w/w loading of oligonucleotide/microspheres (incubated for 16 hrs.). In this case the complexes were tested at 2 and 10 μg/ml, based on the oligonucleotide weight. SAC (PANSORBIN™ (*Staphylococcus aureus* cells, CalBiochem, 1/5000 dilution) and IMPs, SEQ ID NO: 1 and 5'-TCGTCGAACGTTCGAGATG-3' (SEQ ID NO:16) were used as positive controls, and control oligonucleotide, SEQ ID NO: 10, and cells alone were used as negative controls. SAC contains *Staph. Aureus* (Cowan I) cell material. Samples were assayed in two healthy donors in duplicate.

Data presented in Tables 11, 12 and 13 below show that when used alone, the heptameric oligonucleotides and the cationic PLGA microspheres had little activity, if any. In addition, Tables 11, 12 and 13 also demonstrate that mixtures of the 7-mer oligonucleotides had little activity, if any. However, consistent with the previous experiments, heptameric IMP, SEQ ID NO:12, was active in inducing IFN-α and IFN-γ when used under either condition with the cationic PLGA microspheres. Each value in the tables represents the mean of the two readings in parentheses.

TABLE 11

| Sample | IFN-γ (pg/mL) | IFN-α (pg/mL) |
| --- | --- | --- |
| SEQ ID NO: 1 | 621 (73, 1170) | 268 (54, 482) |
| SEQ ID NO: 10 | 37 (7, 66) | 57 (20, 94) |
| Mix of SEQ ID NOs: 12 + 13 | 4 (8, 0) | 0 (0, 0) |
| Mix of SEQ ID NOs: 12, 13, 14, 15 | 97 (46, 148) | 1 (2, 0) |
| SAC | 593 (903, 284) | 4337 (458, 8215) |
| cells alone | 28 (3, 52) | 20 (20, 20) |

TABLE 12

| Sample | oligo + MC incubation# | oligo doses (μg/ml) | IFN-γ (pg/mL) | IFN-α (pg/mL) |
| --- | --- | --- | --- | --- |
| SEQ ID NO: 1 | — | 20 | 27 (39, 14) | 18 (26, 10) |
| SEQ ID NO: 10 | — | 20 | 11 (12, 10) | 10 (10, 10) |
| SEQ ID NO: 16 | — | 20 | 182 (182, 181) | 2597 (2831, 2363) |
| SEQ ID NO: 12 | — | 20 | 10 (10, 10) | 13 (16, 10) |
| SEQ ID NO: 13 | — | 20 | 10 (10, 10) | 16 (22, 10) |
| SEQ ID NO: 15 | — | 20 | 10 (10, 10) | 33 (10, 56) |
| Mix of SEQ ID NOs: 12 + 13 | — | 20 | 10 (10, 10) | 15 (20, 10) |
| cat MC | — | — | 10 (n/a*, 10) | 10 (n/a, 10) |
| SEQ ID NO: 1/cat MC | simult. added | 20 | 1691 (13779, 2002) | 4038 (3748, 4327) |
| SEQ ID NO: 10/cat MC | simult. added | 20 | 154 (173, 135) | 118 (52, 183) |
| SEQ ID NO: 16/cat MC | simult. added | 20 | 2810 (3924, 1695) | 19004 (18008, 20000) |
| SEQ ID NO: 12/cat MC | simult. added | 20 | 621 (n/a, 621) | 6108 (n/a, 6108) |
| SEQ ID NO: 13/cat MC | simult. added | 20 | 16 (10, 22) | 50 (10, 89) |
| SEQ ID NO: 15/cat MC | simult. added | 20 | 10 (10, 10) | 10 (10, 10) |
| SEQ ID NOs: 12 + 13 (Mix)/cat MC | simult. added | 20 | 1041 (712, 1370) | 6915 (7188, 6642) |
| SEQ ID NO: 1/cat MC | 16 hrs. | 2.0 | 524 (466, 583) | 9647 (11524, 7770) |
| SEQ ID NO: 1/cat MC | 16 hrs. | 10 | 646 (492, 800) | 5291 (5843, 4739) |
| SEQ ID NO: 10/cat MC | 16 hrs. | 2.0 | 10 (10, 10) | 24 (38, 10) |
| SEQ ID NO: 10/cat MC | 16 hrs. | 10 | 10 (10, 10) | 71 (131, 10) |
| SEQ ID NO: 12/cat MC | 16 hrs. | 2.0 | 308 (559, 56) | 3629 (5813, 1445) |
| SEQ ID NO: 12/cat MC | 16 hrs. | 10 | 1524 (547, 2500) | 12718 (14807, 10629) |
| SEQ ID NO: 13/cat MC | 16 hrs. | 2.0 | 11 (12, 10) | 15 (20, 10) |
| SEQ ID NO: 13/cat MC | 16 hrs. | 10 | 47 (14, 79) | 66 (122, 10) |
| SEQ ID NO: 15/cat MC | 16 hrs. | 2.0 | 19 (13, 25) | 68 (126, 10) |
| SEQ ID NO: 15/cat MC | 16 hrs. | 10 | 10 (10, 10) | 10 (10, 10) |
| SEQ ID NOs: 12 + 13 (Mix)/cat MC | 16 hrs. | 2.0 | 407 (419, 394) | 5105 (6444, 3766) |

TABLE 12-continued

| Sample | oligo + MC incubation# | oligo doses (µg/ml) | IFN-γ (pg/mL) | IFN-α (pg/mL) |
|---|---|---|---|---|
| SEQ ID NOs: 12 + 13 (Mix)/cat MC | 16 hrs. | 10 | 1739 (1511, 1966) | 8892 (12050, 5733) |
| SAC | — | — | 2500 (2500, 2500) | 12685 (20000, 5369) |
| cells alone | — | — | 10 (10, 10) | 10 (10, 10) |

(#length of time oligonucleotide incubated with cationic MC prior to IMP/MC addition to cells)
(*n/a = not available)

TABLE 13

| Sample | oligo + MC incubation# | oligo doses (µg/ml) | IFN-γ (pg/mL) | IFN-α (pg/mL) |
|---|---|---|---|---|
| SEQ ID NO: 1 | — | 20 | 26 (2, 49) | 9 (0, 18) |
| SEQ ID NO: 10 | — | 20 | 22 (1, 42) | 0 (0, 0) |
| SEQ ID NO: 12 | — | 20 | 3 (1, 5) | 0 (0, 0) |
| SEQ ID NO: 13 | — | 20 | 3 (1, 5) | 0 (0, 0) |
| SEQ ID NO: 15 | — | 20 | 5 (2, 7) | 0 (0, 0) |
| Mix of SEQ ID NOs: 12 + 13 | — | 20 | 4 (1, 6) | 0 (0, 0) |
| cat MC | — | 20 | 22 (3, 40) | 6 (0, 12) |
| SEQ ID NO: 1/cat MC | simult. added | 20 | 147 (9, 284) | 76 (0, 151) |
| SEQ ID NO: 10/cat MC | simult. added | 20 | 6 (2, 10) | 3 (0, 5) |
| SEQ ID NO: 12/cat MC | simult. added | 20 | 522 (43, 1000) | 1175 (349, 2000) |
| SEQ ID NO: 13/cat MC | simult. added | 20 | 25 (3, 46) | 11 (0, 22) |
| SEQ ID NO: 15/cat MC | simult. added | 20 | 36 (2, 70) | 8 (0, 15) |
| SEQ ID NOs: 12 + 13 (Mix)/cat MC | simult. added | 20 | 191 (36, 345) | 882 (300, 1463) |
| SEQ ID NO: 1/cat MC | 16 hrs. | 2.0 | 78 (32, 123) | 970 (162, 1777) |
| SEQ ID NO: 1/cat MC | 16 hrs. | 10 | 87 (9, 164) | 1118 (236, 2000) |
| SEQ ID NO: 10/cat MC | 16 hrs. | 2.0 | 9 (11, 6) | 0 (0, 0) |
| SEQ ID NO: 10/cat MC | 16 hrs. | 10 | 5 (1, 9) | 0 (0, 0) |
| SEQ ID NO: 12/cat MC | 16 hrs. | 2.0 | 62 (25, 99) | 705 (139, 1271) |
| SEQ ID NO: 12/cat MC | 16 hrs. | 10 | 162 (22, 301) | 1115 (230, 2000) |
| SEQ ID NO: 13/cat MC | 16 hrs. | 2.0 | 21 (17, 24) | 33 (19, 46) |
| SEQ ID NO: 13/cat MC | 16 hrs. | 10 | 30 (4, 56) | 0 (0, 0) |
| SEQ ID NO: 15/cat MC | 16 hrs. | 2.0 | 21 (17, 24) | 21 (0, 41) |
| SEQ ID NO: 15/cat MC | 16 hrs. | 10 | 37 (1, 72) | 5 (0, 10) |
| SEQ ID NOs: 12 + 13 (Mix)/cat MC | 16 hrs. | 2.0 | 205 (17, 392) | 486 (48, 924) |
| SEQ ID NOs: 12 + 13 (Mix)/cat MC | 16 hrs. | 10 | 180 (12, 347) | 1058 (116, 2000) |
| SAC | — | — | 1000 (1000, 1000) | 2000 (2000, 2000) |
| cells alone | — | — | 6 (6, 6) | 0 (0, 0) |

(#length of time oligonucleotide incubated with cationic MC prior to IMP/MC addition to cells)

Example 11

Immunomodulation with IMP/MC Complexes

Heptameric oligonucleotides were tested for immunomodulatory activity alone and complexed with cationic PLGA microspheres in the human PBMC assay. The oligonucleotides were premixed with the cationic PLGA microspheres for 15 minutes at room temperature at concentrations were 20 µg/ml and 250 µg/ml, respectively. The human PBMC assay was performed as described in Example 4 and the cationic PLGA microspheres were prepared as described in Example 5. SAC (PANSORBIN™ (*Staphylococcus aureus* cells, CalBiochem, 1/5000 dilution) and IMP SEQ ID NO:1 were used as positive controls, and control oligonucleotide SEQ ID NO:10 and cells alone were used as negative controls. SAC contains *Staph. Aureus* (Cowan I) cell material. Samples were assayed in two healthy donors in duplicate.

The 7-mer phosphorothioate oligonucleotides tested were 5'-TCGTCGA-3' (SEQ ID NO:12), 5'-TCGTTTT-3' (SEQ ID NO:17), 5'-TCGAAAA-3' (SEQ ID NO:18), 5'-TCGCCCC-3' (SEQ ID NO:19), 5'-TCGGGGG-3' (SEQ ID NO:20), 5'-AGATGAT-3' (SEQ ID NO:15) (control).

As shown in Table 14, heptameric oligonucleotides containing a single 5'-TCG were active in inducing IFN-γ and IFN-α in the human PBMC assay when formulated with cationic PLGA microspheres. Oligonucleotides with four or more guanosines in a row are known to form tetraplex structures. SEQ ID NO:20 contains 5 guanosines in a row and was seen as an aggregate by capillary electrophoresis.

TABLE 14

| | IFN-γ (pg/ml) | | | | | IFN-α (pg/ml) | | | | |
|---|---|---|---|---|---|---|---|---|---|---|
| Sample | Ex 1 | Ex 2 | Ex 3 | Ex 4 | mean | Ex 1 | Ex 2 | Ex 3 | Ex 4 | mean |
| SEQ ID NO: 1 | 211 | 131 | 86 | 840 | 317 | 31 | 0 | 15 | 0 | 12 |
| SEQ ID NO: 10 | 0 | 17 | 58 | 98 | 43 | 0 | 0 | 0 | 0 | 0 |

TABLE 14-continued

|  | IFN-γ (pg/ml) | | | | | IFN-α (pg/ml) | | | | |
|---|---|---|---|---|---|---|---|---|---|---|
| Sample | Ex 1 | Ex 2 | Ex 3 | Ex 4 | mean | Ex 1 | Ex 2 | Ex 3 | Ex 4 | mean |
| SEQ ID NO: 12 | 0 | 0 | 14 | 0 | 4 | 0 | 0 | 0 | 0 | 0 |
| SEQ ID NO: 15 | 0 | 0 | 9 | 0 | 2 | 0 | 0 | 0 | 0 | 0 |
| SEQ ID NO: 17 | 0 | 0 | 11 | 0 | 3 | 0 | 0 | 0 | 0 | 0 |
| SEQ ID NO: 18 | 0 | 0 | 11 | 0 | 3 | 0 | 0 | 0 | 0 | 0 |
| SEQ ID NO: 19 | 0 | 0 | 10 | 0 | 3 | 0 | 0 | 0 | 0 | 0 |
| SEQ ID NO: 20 | 41 | 29 | 83 | 114 | 67 | 0 | 0 | 0 | 0 | 0 |
| cat MC | 14 | 0 | 18 | 111 | 36 | 0 | 0 | 0 | 0 | 0 |
| SEQ ID NO: 1/cat MC | 662 | 534 | 689 | 4000 | 1471 | 151 | 62 | 240 | 137 | 148 |
| SEQ ID NO: 10/cat MC | 21 | 22 | 36 | 97 | 44 | 0 | 0 | 25 | 0 | 6 |
| SEQ ID NO: 12/cat MC | 1305 | 912 | 563 | 4000 | 1695 | 755 | 924 | 1881 | 518 | 1020 |
| SEQ ID NO: 15/cat MC | 65 | 15 | 26 | 154 | 65 | 0 | 0 | 9 | 0 | 2 |
| SEQ ID NO: 17/cat MC | 2953 | 1316 | 1309 | 991 | 1642 | 702 | 1032 | 769 | 708 | 603 |
| SEQ ID NO: 18/cat MC | 740 | 430 | 350 | 1337 | 714 | 380 | 407 | 802 | 211 | 450 |
| SEQ ID NO: 19/cat MC | 1046 | 974 | 727 | 2543 | 1323 | 607 | 598 | 859 | 359 | 606 |
| SEQ ID NO: 20/cat MC | 512 | 96 | 149 | 579 | 334 | 81 | 0 | 39 | 185 | 76 |
| SAC | 2689 | 117 | 914 | 4000 | 1930 | 155 | 19 | 261 | 119 | 139 |
| cells alone | 0 | 0 | 14 | 0 | 0 | 0 | 0 | 0 | 0 | 0 |

Example 12

Immunomodulation with Phosphodiester IMP/MC Complexes

Immunomodulatory activity in the human PBMC assay of single-stranded (ss) and double-stranded (ds) phosphodiester (PO) IMPs was compared to that of ss phosphothioate (PS) IMP. In the assay, the IMPs were presented to the cells alone or complexed with cationic PLGA microspheres. The human PBMC assay was performed as described in Example 4. Cationic PLGA microspheres and IMP/MC complexes were prepared as described in Example 5. SAC (PANSORBIN™ (Staphylococcus aureus cells, CalBiochem, 1/5000 dilution) and IMPs SEQ ID NO:1 and SEQ ID NO:16, were used as positive controls, and control oligonucleotide SEQ ID NO:10 and cells alone were used as negative controls. SAC contains Staph. Aureus (Cowan I) cell material. Samples were assayed in two healthy donors in duplicate.

As shown in Table 15 below, neither ss nor ds phosphodiester (PO) IMPs (SEQ ID NO:1 and SEQ ID NO:16) showed significant activity in the human PBMC assay when used alone at the concentrations tested. However, when ss or ds phosphodiester (PO) IMP SEQ ID NO:1 was complexed with cationic PLGA microspheres, these IMP/MC complexes were as active as complexes with ss phosphorothioate (PS) IMP SEQ ID NO:1 in inducing IFN-γ and IFN-α in the human PBMC assay.

TABLE 15

| Sample | PS or PO | oligo (µg/ml) | IFN-γ (pg/ml) | | | IFN-α (pg/ml) | | |
|---|---|---|---|---|---|---|---|---|
|  |  |  | Ex 1 | Ex 2 | mean | Ex 1 | Ex 2 | mean |
| SEQ ID NO: 1 | PS | 20 | 72 | 63 | 68 | 4 | 632 | 318 |
| SEQ ID NO: 10 | PS | 20 | 31 | 2 | 17 | 0 | 10 | 5 |
| cat MC |  | 0 | 44 | 110 | 77 | 97 | 324 | 211 |
| SEQ ID NO: 1/cat MC | PS | 2 | 1103 | 844 | 974 | 932 | 4579 | 2756 |
| SEQ ID NO: 1/cat MC | PS | 10 | 1103 | 1103 | 1103 | 1358 | 3901 | 2630 |
| ss SEQ ID NO: 1/cat MC | PO | 2 | 1103 | 1103 | 1103 | 1334 | 3027 | 2181 |
| ss SEQ ID NO: 1/cat MC | PO | 10 | 1103 | 1103 | 1103 | 655 | 1817 | 1236 |
| ss SEQ ID NO: 1/cat MC | PO | 25 | 935 | 935 | 935 | 476 | 1819 | 1147 |
| ds SEQ ID NO: 1/cat MC | PO | 2 | 1103 | 1103 | 1103 | 1572 | 4207 | 2890 |
| ds SEQ ID NO: 1/cat MC | PO | 10 | 1103 | 1103 | 1103 | 1418 | 2779 | 2098 |
| ds SEQ ID NO: 1/cat MC | PO | 25 | 1103 | 385 | 744 | 1125 | 2703 | 1914 |
| SEQ ID NO: 1 | PS | 100 | 38 | 46 | 42 | 43 | 576 | 309 |
| ds SEQ ID NO: 1 | PO | 40 | 9 | 2 | 6 | 11 | 20 | 16 |
| ds SEQ ID NO: 1 | PO | 100 | 5 | 0 | 3 | 23 | 5 | 14 |
| ss SEQ ID NO: 1 | PO | 20 | 0 | 0 | 0 | 0 | 0 | 0 |
| ss SEQ ID NO: 1 | PO | 100 | 0 | 0 | 0 | 0 | 0 | 0 |
| ds SEQ ID NO: 16 | PO | 40 | 0 | 0 | 0 | 0 | 0 | 0 |
| ds SEQ ID NO: 16 | PO | 100 | 5 | 0 | 3 | 0 | 0 | 0 |
| SAC |  |  | 1103 | 895 | 999 | 1572 | 549 | 1060 |
| cells alone |  |  | 0 | 0 | 0 | 0 | 5 | 2 |

Example 13

Effects of IMP/MC Formulation in Cell Proliferation Assay

Human PBMC were isolated from heparanized blood from two normal subjects. Some PBMCs were held in reserve while the remainder was incubated with CD19+ MACS beads from Miltenyi. These cells were then passed through a magnet, separating out the CD19+ B cells through positive selection. This population was determined to be >98% CD19+ through FACS analysis. B cells were then cultured at $1 \times 10^5$/200 µl/well in 96-well round-bottomed plates. PBMCs were also cultured, but at $2 \times 10^5$/200 µl/well. Cells were stimulated in triplicate with 2 µg/ml oligonucleotide either alone or with 100 µg/ml cationic PLGA microspheres (premixed for 15 minutes at room temperature). The culture period was 48 hours at 37° C. At the end of the culture period, the plates were pulsed with ³H-thymidine, 1 µCi/well, and incubated for an additional 8 hours. Then the plates were harvested using standard liquid scintillation techniques and data collected in counts per minutes (cpm).

As shown in Table 16 below, the 7-mer, SEQ ID NO:12, induces less human B cell and PBMC proliferation than the control sequence, SEQ ID NO:10, when used alone. However, when the 7-mer, SEQ ID NO:12, is formulated with cationic PLGA microspheres, it is able to generate similar amounts of proliferation as IMP, SEQ ID NO:1. The values in the table for experiments 1 and 2 represent the cpm mean of three wells.

TABLE 16

| Sample | cells | Ex 1 (cpm) | Ex 2 (cpm) | mean |
| --- | --- | --- | --- | --- |
| SEQ ID NO: 1 | B cells | 30922 | 24976 | 27949 |
| SEQ ID NO: 10 | B cells | 5916 | 3735 | 482e5 |

TABLE 16-continued

| Sample | cells | Ex 1 (cpm) | Ex 2 (cpm) | mean |
| --- | --- | --- | --- | --- |
| SEQ ID NO: 12 | B cells | 697 | 572 | 634 |
| SEQ ID NO: 12/cat MC | B cells | 23469 | 5958 | 14714 |
| cells alone | B cells | 605 | 379 | 492 |
| SEQ ID NO: 1 | PBMC | 24635 | 22599 | 23617 |
| SEQ ID NO: 10 | PBMC | 8556 | 10033 | 9295 |
| SEQ ID NO: 12 | PBMC | 5063 | 1330 | 3197 |
| SEQ ID NO: 12/cat MC | PBMC | 25095 | 27228 | 26162 |
| cells alone | PBMC | 2444 | 1949 | 2196 |

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

What is claimed is:

1. A method of modulating an immune response in an individual comprising administering to an individual a composition comprising an immunomodulatory polynucleotide/microcarrier (IMP/MC) complex, said complex comprising a polynucleotide linked to a biodegradable microcarrier (MC), wherein said polynucleotide comprises an immunostimulatory sequence (ISS) 5'-C, G-3', wherein the C is an unmethylated cytosine, wherein the polynucleotide is greater than 6 nucleotides and less than about 200 nucleotides in length, and wherein said MC is less than 10 μm in size, in an amount sufficient to modulate an immune response in said individual.

2. The method of claim 1, wherein said microcarrier is a solid phase microcarrier.

3. The method of claim 1, wherein said microcarrier is a liquid phase microcarrier.

4. The method of claim 1, wherein said polynucleotide is covalently linked to said microcarrier.

5. The method of claim 1, wherein said polynucleotide is non-covalently linked to said microcarrier.

6. The method of claim 1, wherein said complex is antigen-free.

7. The method of claim 1, wherein a Th1-type immune response is stimulated.

8. The method of claim 1, wherein a Th2-type immune response is suppressed.

9. The method of claim 1, wherein interferon-gamma (IFN-γ) is increased in said individual.

10. The method of claim 1, wherein interferon-alpha (IFN-α) is increased in said individual.

11. The method of claim 1, wherein levels of IgE is reduced in said individual.

12. The method of claim 1, wherein said polynucleotide comprises the immunostimulatory sequence 5'-T, C, G-3'.

13. The method of claim 12, wherein said polynucleotide comprises the immunostimulatory sequence 5'-TCGX$_1$X$_2$X$_3$X$_4$-3' or the immunostimulatory sequence 5'-X$_1$TCGX$_2$X$_3$X$_4$-3', wherein X$_1$, X$_2$, X$_3$, X$_4$ are nucleotides.

14. The method of claim 13, wherein the polynucleotide comprises the immunostimulatory sequence 5'-TCGTCGX$_1$-3', wherein X$_1$ is a nucleotide.

15. The method of claim 13, wherein said polynucleotide comprises an immunostimulatory sequence selected from the group consisting of 5'-TCGTCGA-3', 5'-TCGAAAA-3', 5'-TCGCCCC-3', 5'-TCGGGGG-3' and 5'-TCGTTTT-3'.

16. The method of claim 1, wherein said polynucleotide comprises the immunostimulatory sequence 5'-C, G, pyrimidine, pyrimidine, C, G-3'.

17. The method of claim 1, wherein said polynucleotide comprises the immunostimulatory sequence 5'-purine, purine, C, G, pyrimidine, pyrimidine, C, G-3'.

18. The method of claim 12, wherein said polynucleotide comprises the immunostimulatory sequence SEQ ID NO:1.

19. The method of any of claims 1, or 12-15 wherein said polynucleotide is 7 nucleotides in length.

20. The method of any of claims 1, or 12-15 wherein said composition further comprises an antigen.

21. The method of claim 20, wherein said antigen is an allergen.

22. The method of claim 1, wherein said polynucleotide comprises a phosphate backbone modification.

23. The method of claim 22, wherein said phosphate backbone modification is a phosphorothioate.

* * * * *

SEQUENCE LISTING

```
<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 1
tgactgtgaa cgttcgagat ga                                              22

<210> SEQ ID NO 2
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 2
tgaccgtgaa cgttcgagat ga                                              22

<210> SEQ ID NO 3
<211> LENGTH: 23
<212> TYPE: DNA
<213> ORGANISM: Artificial Sequence
<220> FEATURE:
<223> OTHER INFORMATION: Polynucleotide containing CG

<400> SEQUENCE: 3
tcatctcgaa cgttccacag tca                                             23

<210> SEQ ID NO 4
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 4
```
tgactgtgaa cgttccagat ga                                                    22

<210> SEQ ID NO 5
<211> LENGTH: 26
<212> TYPE: DNA
<213> ORGANISM: Artificial Sequence
<220> FEATURE:
<223> OTHER INFORMATION: Polynucleotide containing CG

<400> SEQUENCE: 5
tccataacgt tcgcctaacg ttcgtc                                                26

<210> SEQ ID NO 6
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11
<223> OTHER INFORMATION: n= 5-bromocytosine

<400> SEQUENCE: 6
tgactgtgaa ngttccagat ga                                                    22

<210> SEQ ID NO 7
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11
<223> OTHER INFORMATION: n= 5-bromocytosine

<400> SEQUENCE: 7
tgactgtgaa ngttcgagat ga                                                    22

<210> SEQ ID NO 8
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<220> FEATURE:
<221> NAME/KEY: misc_feature
<222> LOCATION: 11, 15
<223> OTHER INFORMATION: n= 5-bromocytosine

<400> SEQUENCE: 8
tgactgtgaa ngttngagat ga                                                    22

<210> SEQ ID NO 9
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 9
tgactgtgaa ggttagagat ga                                                    22

<210> SEQ ID NO 10
<211> LENGTH: 22
<212> TYPE: DNA
<213> ORGANISM: Artificial Sequence
<220> FEATURE:

```
<223> OTHER INFORMATION: Polynucleotide not containing CG

<400> SEQUENCE: 10
tgactgtgaa ccttagagat ga                                              22

<210> SEQ ID NO 11
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 11
tcactctctt ccttactctt ct                                              22

<210> SEQ ID NO 12
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 12 tcgtcga                                                                7

<210> SEQ ID NO 13
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 13 acgttcg                                                                7

<210> SEQ ID NO 14
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 14 atctcga                                                                7

<210> SEQ ID NO 15
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 15 agatgat                                                                7

<210> SEQ ID NO 16
<211> LENGTH: 19
<212> TYPE: DNA
<213> ORGANISM: Artificial Sequence
<220> FEATURE:
<223> OTHER INFORMATION: Polynucleotide containing CG

<400> SEQUENCE: 16
tcgtcgaacg ttcgagatg                                                  19

<210> SEQ ID NO 17
```

-continued

```
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 17 tcgtttt                                                                7

<210> SEQ ID NO 18
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 18 tcgaaaa                                                                7

<210> SEQ ID NO 19
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 19 tcgcccc                                                                7

<210> SEQ ID NO 20
<211> LENGTH: 7
<212> TYPE: DNA
<213> ORGANISM: Artificial Sequence
<220> FEATURE:
<223> OTHER INFORMATION: Polynucleotide containing CG

<400> SEQUENCE: 20 tcggggg                                                                7

<210> SEQ ID NO 21
<211> LENGTH: 11
<212> TYPE: DNA
<213> ORGANISM: Artificial Sequence
<220> FEATURE:
<223> OTHER INFORMATION: Polynucleotide containing CG

<400> SEQUENCE: 21
tcgagcgttc t                                                          11

<210> SEQ ID NO 22
<211> LENGTH: 20
<212> TYPE: DNA
<213> ORGANISM: Artificial Sequence
<220> FEATURE:
<223> OTHER INFORMATION: Polynucleotide containing CG

<400> SEQUENCE: 22
atcgactctc gagcgttctc                                                 20

<210> SEQ ID NO 23
<211> LENGTH: 24
<212> TYPE: DNA
```

```
<213> ORGANISM: Artificial Sequence
<220> FEATURE:
<223> OTHER INFORMATION: Polynucleotide containing CG

<400> SEQUENCE: 23
tcgtcgtttt gtcgtttgt cgtt                                    24
```